US010010520B2

(12) United States Patent
Cheng et al.

(10) Patent No.: US 10,010,520 B2
(45) Date of Patent: Jul. 3, 2018

(54) COMBINED APPLICATION OF ISOTHIOCYANATE COMPOUND AND ANTI-CANCER MEDICINE

(71) Applicant: JC (WUXI) COMPANY, INC., Wuxi, Jiangsu (CN)

(72) Inventors: Jingcai Cheng, Jiangsu (CN); Chunxia Zhang, Jiangsu (CN); Zhiwei Cheng, Jiangsu (CN)

(73) Assignee: JC (Wuxi) Company, Inc., Wuxi, Jiangsu (CN)

( * ) Notice: Subject to any disclaimer, the term of this patent is extended or adjusted under 35 U.S.C. 154(b) by 0 days.

(21) Appl. No.: 14/912,239

(22) PCT Filed: Aug. 13, 2014

(86) PCT No.: PCT/CN2014/084324
§ 371 (c)(1),
(2) Date: May 11, 2016

(87) PCT Pub. No.: WO2015/021929
PCT Pub. Date: Feb. 19, 2015

(65) Prior Publication Data
US 2016/0250175 A1  Sep. 1, 2016

(30) Foreign Application Priority Data

Aug. 13, 2013 (CN) .......................... 2013 1 0352414
Aug. 20, 2013 (CN) .......................... 2013 1 0364101
Jul. 18, 2014 (CN) .......................... 2014 1 0346419

(51) Int. Cl.
*A61K 31/16* (2006.01)
*A61K 31/33* (2006.01)
*A61K 31/28* (2006.01)
*A61K 31/58* (2006.01)
*A61K 31/415* (2006.01)
*A61K 38/22* (2006.01)
*A61K 31/26* (2006.01)
*A61K 31/436* (2006.01)
*A61K 31/165* (2006.01)
*A61K 31/44* (2006.01)
*A61K 31/475* (2006.01)
*A61K 31/4985* (2006.01)
*A61K 31/506* (2006.01)
*A61K 31/517* (2006.01)
*A61K 31/69* (2006.01)
*A61K 31/167* (2006.01)
(Continued)

(52) U.S. Cl.
CPC .............. *A61K 31/26* (2013.01); *A61K 31/16* (2013.01); *A61K 31/165* (2013.01); *A61K 31/167* (2013.01); *A61K 31/17* (2013.01); *A61K 31/282* (2013.01); *A61K 31/33* (2013.01); *A61K 31/337* (2013.01); *A61K 31/4164* (2013.01); *A61K 31/4166* (2013.01); *A61K 31/4184* (2013.01); *A61K 31/436* (2013.01); *A61K 31/437* (2013.01); *A61K 31/44* (2013.01); *A61K 31/4412* (2013.01); *A61K 31/4439* (2013.01); *A61K 31/475* (2013.01); *A61K 31/4745* (2013.01); *A61K 31/4985* (2013.01); *A61K 31/506* (2013.01); *A61K 31/517* (2013.01); *A61K 31/519* (2013.01); *A61K 31/58* (2013.01); *A61K 31/69* (2013.01); *A61K 31/704* (2013.01); *A61K 31/7068* (2013.01); *A61K 31/7076* (2013.01); *A61K 33/24* (2013.01); *A61K 33/36* (2013.01); *A61K 38/10* (2013.01); *A61K 38/14* (2013.01)

(58) Field of Classification Search
CPC ........................... A61K 31/282; A61K 31/145
USPC ................ 514/599, 183, 492, 176, 391, 9.7
See application file for complete search history.

(56) References Cited

U.S. PATENT DOCUMENTS 7,514,078 B2 * 4/2009 Bander ............ A61K 47/48638
424/133.1
8,039,511 B2  10/2011 Cheng et al.
(Continued)

FOREIGN PATENT DOCUMENTS

CA      2630262     5/2007
CN      1724516     1/2006
(Continued)

OTHER PUBLICATIONS

CN 101167741 (A) 2008, Machine Translation.*
(Continued)

*Primary Examiner* — Shengjun Wang
(74) *Attorney, Agent, or Firm* — Hamre, Schumann, Mueller & Larson, P.C.

(57) ABSTRACT

The present invention relates to a combined application of isothiocyanate compounds and anti-cancer drugs, in particular to a composition, comprising: (A) a therapeutically effective amount of a first active ingredient, the first active ingredient being an isothiocyanate compound or derivative thereof; (B) a therapeutically effective amount of a second active ingredient, the second active ingredient being anti-cancer drugs effecting or influencing DNA, kinase inhibitor anti-cancer drugs or endocrine therapy hormonal anti-cancer drugs, the mass ratio of the first active ingredient and the second active ingredient being from 1:10000 to 10000:1. Also disclosed are an active ingredient composition, kit, pharmaceutical composition and uses thereof in the preparation of anti-cancer drugs. The composition, active ingredient composition and kit have excellent effect of inhibiting the growth of cancer cells.

10 Claims, No Drawings

(51) Int. Cl.

| | | |
|---|---|---|
| A61K 31/17 | (2006.01) | |
| A61K 31/282 | (2006.01) | |
| A61K 31/337 | (2006.01) | |
| A61K 31/4164 | (2006.01) | |
| A61K 31/4166 | (2006.01) | |
| A61K 31/4184 | (2006.01) | |
| A61K 31/437 | (2006.01) | |
| A61K 31/4412 | (2006.01) | |
| A61K 31/4439 | (2006.01) | |
| A61K 31/4745 | (2006.01) | |
| A61K 31/519 | (2006.01) | |
| A61K 31/704 | (2006.01) | |
| A61K 31/7068 | (2006.01) | |
| A61K 31/7076 | (2006.01) | |
| A61K 33/24 | (2006.01) | |
| A61K 33/36 | (2006.01) | |
| A61K 38/10 | (2006.01) | |
| A61K 38/14 | (2006.01) | |

(56) References Cited

U.S. PATENT DOCUMENTS

| | | |
|---|---|---|
| 8,410,170 B2 | 4/2013 | Cheng et al. |
| 2008/0124407 A1 | 5/2008 | Eaton et al. |
| 2013/0079401 A1 | 3/2013 | Chen et al. |

FOREIGN PATENT DOCUMENTS

| | | |
|---|---|---|
| CN | 101091705 | 12/2007 |
| CN | 101167741 | 4/2008 |
| CN | 101897691 | 12/2010 |
| CN | 104117064 | 10/2014 |
| CN | 104173272 | 12/2014 |
| CN | 104415332 | 3/2015 |
| EP | 1961418 | 8/2008 |
| JP | 5308160 | 10/2013 |
| WO | 2010065329 A2 | 6/2010 |
| WO | WO2010/0065329 A2 * | 6/2010 |

OTHER PUBLICATIONS

Hussain et al. "Concurrent Sulforaphane and Eugenol induces Differential Effects on human cervical cancer", Integrative Cancer Therapies, 2012, vol. 11, No. 2, pp. 154-165.*
International search report for international application No. PCT/CN2014/084324, dated Dec. 8, 2014 (4 pages, including English translation).
V. Rausch et al., "Synergistic Activity of Sorafenib and Sulforaphane Abolishes Pancreatic Cancer Stem Cell Characteristics," Cancer Research, vol. 70, No. 12 (Jun. 15, 2010), p. 5004-5013.
Dong et al., "Phenethyl Isothiocyanate Sensitizes Androgen-independent Human Prostate Cancer Cells to Docetaxel-Induced Apoptosis In Vitro and In Vivo," Pharm Res, vol. 27, No. 4 (Apr. 2010), p. 722-731.
Wang et al., "Enhanced cytotoxicity of mitomycin C in human tumour cells with inducers of DT-diaphorase", British Journal of Cancer, 1999; 80(8), pp. 1223-1230, 8 pages.
Tseng et al., "Effect of Organic Isothiocyanates on the P-Glycoprotein- and MRP1-Mediated Transport of Daunomycin and Vinblastine", Pharmaceutical Research, Oct. 2002, vol. 19, Issue 10, pp. 1509-1515, 8 pages.
Ji et al., "Effect of Organic Isothiocyanates on Breast Cancer Resistance Protein (ABCG2)-Mediated Transport" Pharmaceutical Research, Dec. 2004, vol. 21, Issue 12, pp. 2261-2269, 10 pages.
Mukherjee et al., "Isothiocyanates sensitize the effect of chemotherapeutic drugs via modulation of protein kinase C and telomerase in cervical cancer cells", Molecular and Cellular Biochemistry, 2009, DOI 10.1007/s11010-009-0095-4, pp. 9-22, 14 pages.
Trachootham et al.; "Effective elimination of fludarabine-resistant CLL cells by PEITC through a redox-mediated mechanism", Blood, Sep. 1, 2008, vol. 112, No. 5, pp. 1912-1922, 12 pages.
Kallifatidis et al., "Sulforaphane increases drug-mediated cytotoxicity toward cancer stem-like cells of pancreas and prostate", The American Society of Gene & Cell Therapy, Targeting of Pancreatic Cancer Stem Cells, www.moleculartherapy.org, vol. 19, No. 1, Jan. 2011, pp. 188-195, 8 pages.
Kaminski et al., "Sulforaphane potentiates oxaliplatin-induced cell growth inhibition in colorectal cancer cells via induction of different modes of cell death", Cancer Chemother Pharmacol, May 2011, pp. 1167-1178, DOI 10.1007/s00280-010-1413-y, 12 pages.
Wang et al., "Phenethyl isothiocyanate sensitizes human cervical cancer cells to apoptosis induced by cisplatin", Mol Nutr Food Res. Oct. 2011; 55(10), pp. 1572-1581, DOI:10.1002/mnfr.201000560, 18 pages.
Liu et al., "Synergistic effect of paclitaxel and epigenetic agent phenethyl isothiocyanate on growth inhibition, cell cycle arrest and apoptosis in breast cancer cells", Cancer Cell International, 2013, 13:10, http://www.cancerci.com/content/13/1/10, 8 apges.
Qazi et al., "Anticancer Activity of a Broccoli Derivative, Sulforaphane, in Barrett Adenocarcinoma: Potential Use in Chemoprevention and as Adjuvant in Chemotherapy1", Translational Oncology, Dec. 2010; vol. 3 No. 6, pp. 389-399, 11 pages.
Suppipat et al., "Targeting AKT Signaling in Pediatric Acute Lymphoblastic Leukemia with Sulforaphane", The American Society of Hematology, 2011, vol. 118 No. 21, 3 pages.
Xiao et al., "Phenethyl isothiocyanate sensitizes androgen-independent human prostate cancer cells to Docetaxel-Induced Apoptosis In Vitro and In Vivo", Pharmaceutical Research, vol. 27, No. 4, Apr. 2010, pp. 722-731, 10 pages.
Minarini et al., "Exploring the effects of isothiocyanates on chemotherapeutic drugs", Expert Opinion on Drug Metabolism & Toxicology, vol. 10, Issue 1, 2014, 15 pages.
Rausch et al., "Synergistic activity of sorafenib and sulforaphane abolishes pancreatic cancer stem cell characteristics", Cancer Res; 70 (12), Jun. 15, 2010, 11 pages.
Communication issued in European Patent Application No. 14836229.6, dated Jul. 12, 2017, 9 pages.
The supplementary European Search Report issued in European Patent Application No. 14836229.6, dated Oct. 10, 2016, 22 pages.

* cited by examiner

COMBINED APPLICATION OF ISOTHIOCYANATE COMPOUND AND ANTI-CANCER MEDICINE

FIELD OF THE INVENTION

The present invention relates to the field of pharmaceutical formulation, in particular relates to a composition, kit and pharmaceutical composition comprising isothiocyanates or derivatives thereof, and DNA-effecting or influencing anticancer drugs, kinase-inhibiting anticancer drugs or hormonal anticancer drugs for endocrine therapy, and their use in the preparation of medicaments for treating cancer.

BACKGROUND OF THE INVENTION

The present application is a subsequent patent application of CN200510040865.1, CN200610126892.5, CN200910052231.6, CN201310205609.8, CN201310352414.6, CN201310364101.2, CN201410346419.2, U.S. Pat. No. 8,039,511B2, U.S. Pat. No. 8,410,170B2, EP06817815.1, CA2630262 and JP5308160.

Cancer is a major disease which threatens human health. The treatment of cancer is always closely concerned all over the world. Chemotherapeutic drugs can nonspecifically block cell division, thus resulting in cell death; however, they also destroy normal cells of a body when killing tumor cells. It is an urgent need to reduce side effects of chemotherapeutics and enhance therapeutic effects of the chemotherapeutics.

Anti-cancer drugs, which effect or influence DNAs, such as alkylating agent anticancer drugs, are of broad-spectrum anti-tumor effect, while of poor selectivity as its main drawback. It is of strong toxicity to vigorous growing normal cells, such as bone marrow, gastrointestinal epithelium and reproductive system, and can cause leukopenia and thrombocytopenia, aplastic anemia, or whole blood inhibition. Gastrointestinal reactions comprise nausea, vomiting, inflammation and ulcers, etc. For example, inhibition of hematopoietic function of bone marrow, gastrointestinal reactions and strong toxicity to heart are the major adverse reactions of antibiotic antitumor drugs. Patients are in an urgent need of reducing the toxicity of anticancer drugs of this type, reducing clinical doses, and finding a reliable combination regimen.

Cytotoxic drugs often have limited therapeutic spectrum, and can lead to treatment-related adverse reactions. While targeting specific pathways can prevent tumor growth as well as reduce toxicity to normal cells. The development of anticancer drugs has been transited from random selection by experience to reasonable drug development targeting specific cell dysfunction according to mechanism. Many drugs developed by targeting strategy have been used in clinical and achieved good results. With the development of molecular biology, tumor molecular targeted therapy research based on tumor molecular mechanisms has been significantly progressed. Currently, protein kinase inhibitors are the focus of drug research for cancer targeted therapy, in which survival and proliferation of tumor cells and progression of disease are affected by blocking molecule signaling pathways in cells. However, kinase inhibitors used alone are of limited efficiency and there are some side effects. Therefore, the clinical treatment of cancer is in urgent need of drug combinations which are of significant therapeutic effects and low toxic side effects.

Prostate cancer (PCa) is the most common malignant tumor of reproductive system in male, incidence of which now ranks the third in male cancer, and rapidly increases in recent years. Prostate cancer is seriously affecting the life quality and expectancy of domestic male citizens over 50 years old. Because of inadequate awareness and attention to prostate cancer, early examination, early detection and early treatment (while in developed countries, examinations about prostate cancer are must projects in health check of elderly male citizens) of prostate cancer are seldomly conducted, and most of discovered cases of prostate cancer in China are advanced cases, which brought great difficulty for the effective treatment, and has become one of the key areas of concern of Urology.

Most prostate cancer patients in the early and medium-term onset can be treated by surgery, radiation therapy and drug treatment, while patients in advanced stage can be treated by hormonal therapy or orchiectomy treatment. In terms of therapeutic efficacy and side effects, all of the methods are of some limitations. For example, after surgery, side effects such as difficulty in urinating and sexual disorders occur in most patients, which would likely last for several years.

Advanced stage prostate cancer patients cannot be treated by excision, so endocrine therapy is the main treating method. The main method of endocrine treatment comprises drug or surgical castration, androgen blockade to target cells, 5α-reductase inhibitors, anti-adrenal secretion drugs, etc. Castration or combination therapy are initially effective for most patients, but after 14 to 30 months, lesions in almost all the patients will gradually develop into hormone-independent prostate cancer, which shows resistance to endocrine therapy. During early stage of hormone-independence, second-line endocrine therapy is still valid in some patients, which is known as androgen-independent prostate cancer (AIPC), while prostate cancer, in which the second-line endocrine therapy is invalid or lesions continue to develop during second-line hormonal therapy, is known as Hormone Refractory Prostate Cancer (HRPC). The mechanisms of AIPC and HRPC are still unknown at present, and there is no effective therapeutic, which makes it a worldwide problem as well as the main cause of death of patients with prostate cancer. It is the key point and challenge to look for new anti-cancer drugs for enhancing the effect of endocrine therapy, thereby effectively delaying or reversing AIPC and HRPC.

Isothiocyanates (ITCs) are derived from vegetables which are most commonly consumed by human. Domestic and foreign colleagues have studied them for decades, and found by in vivo animal experiments that ITCs are effective in preventing many types of cancers, while the epidemiological studies also confirmed that the intake of vegetables containing ITCs can effectively reduce the risk of cancer in human being. Basic studies have shown that isothiocyanates are dual inhibitors which can inhibit abnormal DNA methylation as well as histone deacetylase, and useful for the treatment and prevention of cancers.

SUMMARY OF THE INVENTION

The object of the present invention is to provide a composition, kit or combination of active ingredients for the treatment of cancer, and their use in the preparation of medicines for the treatment of cancer. The therapeutic effects on cancer are enhanced by the synergistic effect of the two active ingredients.

In the first aspect of the present invention, a composition is provided, wherein the composition comprises:

(A) therapeutically effective amount of a first active ingredient, wherein the first active ingredient is isothiocyanates or derivatives thereof;

(B) therapeutically effective amount of a second active ingredient, wherein the second active ingredient is DNA-effecting or influencing anticancer drugs, kinase-inhibiting anticancer drugs or hormonal anticancer drugs for endocrine therapy.

In another preferred embodiment, the composition consists of (A) therapeutically effective amount of a first active ingredient, wherein the first active ingredient is an isothiocyanates compound or the derivatives thereof; and (B) therapeutically effective amount of a second active ingredient, wherein the second active ingredient is a DNA-effecting or influencing anticancer drug, a kinase-inhibiting anticancer drug or a hormonal anticancer drug for endocrine therapy.

In another preferred embodiment, the content of the first active ingredient is in a range of 0.01% to 99.99%, based on the total weight of the active ingredients in the composition; preferably from 0.1% to 99.9%; more preferably from 1% to 99%; more preferably from 10% to 99%; more preferably from 20% to 99%; more preferably from 30% to 99%, more preferably from 40% to 99%.

In another preferred embodiment, the content of the second active ingredient is in a range of 0.01% to 99.99%, based on the total weight of the active ingredients in the composition; preferably from 0.1% to 99.9%; more preferably from 1% to 99%; more preferably from 1% to 90%; more preferably from 1% to 80%; more preferably from 1% to 70%, more preferably from 1% to 60%.

In another preferred embodiment, the first active ingredient is a compound of formula (I) or a derivative of formula (II):

A-NCS  (I)

Wherein in formula (I),

NCS is an isothiocyanate group;

A is —XR$_1$ or —CR$_2$R$_3$R$_4$; wherein X is —(CH$_2$)n-, n is an integer of 0-6;

R$_1$ is a methyl, t-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, t-octyl, chlorine atom, trimethylsilyl, or substituted or unsubstituted phenyl;

Wherein "substituted" means that one or more Hs in a group are substituted by substituents selected from the following group: a halogen, methyl, bromomethyl, ethyl, methoxy, nitro, azido, trifluoromethyl, difluoromethoxy, methylthio, cyano, trifluoromethoxy, trifluoromethylthio, t-butoxycarbonyl, and ethoxycarbonyl;

R$_2$, R$_3$, R$_4$ are independently H, phenyl or C$_{1-3}$ alkyl;

  (II)

Wherein in formula (II):

A is defined as in formula (I);

R$_5$ is a hydrogen, or a group derived from the following compounds, wherein the group is connected to the carbon atom of

via a sulphur atom: N-acetylcysteine, glutathione, cysteine (C$_{1-6}$ alkyl) ester, cysteinyl amino acid and cysteinyl amino acid (C$_{1-6}$ alkyl) ester.

In another preferred embodiment, the amino acid is selected from: glycine, glutamic acid, serine, alanine or methionine.

In another preferred embodiment, the first active ingredient is selected from the following group: isothiocyanates, adducts of isothiocyanate and N-acetyl cysteine, or a combination thereof; wherein the isothiocyanates are selected from the following group: ethyl phenyl isothiocyanate, cyclohexyl isothiocyanate, 4-methoxybenzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanate, 1-isothiocyanate-4-methanesulfonyl butane (sulforaphane), isothiocyanate α-methyl benzyl ester, hexyl isothiocyanate, isothiocyanate methyl cyclohexyl ester, 1-naphthyl isothiocyanate, 2-chlorophenyl isothiocyanate, 2-bromophenyl isothiocyanate, 3-chlorophenyl isothiocyanate, 3-bromophenyl isothiocyanate, 3-nitrophenyl isothiocyanate, 4-azido phenyl isothiocyanate, 4-fluorophenyl isothiocyanate, 4-chlorophenyl isothiocyanate, 4-bromophenyl isothiocyanate, 4-nitrophenyl isothiocyanate, ethoxycarbonyl isothiocyanate, tert-octyl isothiocyanate, p-tolyl isothiocyanate, benzoyl isothiocyanate, o-tolyl isothiocyanate, m-tolyl isothiocyanate, 2,3,4-trifluorophenyl isothiocyanate, 2,5-dimethoxyphenyl isothiocyanate, 2-(4-morpholino) ethyl isothiocyanate, 2-(trifluoromethyl) phenyl isothiocyanate, 2-(difluoromethoxy) phenyl isothiocyanate, 2-(methylthio) phenyl isothiocyanate, 2-fluoro-5-(trifluoromethyl) phenyl isothiocyanate, 3,5-bis(trifluoromethyl) phenyl isothiocyanate, 3-(4-morpholinyl) propyl isothiocyanate, 3-(trifluoromethyl) phenyl isothiocyanate, 3-(diethylamino) propyl isothiocyanate, 3-(methylthio) propyl isothiocyanate, 3-(methylthio) phenyl isothiocyanate, 3-cyano-phenyl isothiocyanate, 4-(trifluoromethyl) phenyl isothiocyanate, 4-(trifluoromethoxy) phenyl isothiocyanate, 4-(trifluoromethylthio) phenyl isothiocyanate, 4-(difluoromethoxy) phenyl isothiocyanate, 4-(methylthio) phenyl isothiocyanate, 4-cyano phenyl isothiocyanate, 4-bromo-2-fluorophenyl isothiocyanate, 4-methoxy-phenyl isothiocyanate, methallyl isothiocyanate, ethyl 2-(4-isothiocyanato-phenoxy) toluenesulfonate, 2-chloro-ethyl isothiocyanate, (2-fluorophenyl) isothiocyanate, (3-fluorophenyl) isothiocyanate, butyl isothiocyanate, trimethylsilyl isothiocyanate, propyl isothiocyanate, ethyl isothiocyanate, tert-butyl isothiocyanate, isopropyl isothiocyanate, allyl isothiocyanate, methyl isothiocyanate, phenethyl isothiocyanate, benzyl isothiocyanate, phenyl isothiocyanate, 2,4,5-trichloro phenyl isothiocyanate, 2,4,6-trichloro-phenyl isothiocyanate, 2,4-difluoro-phenyl isothiocyanate, 2,5-difluoro-phenyl isothiocyanate, 2,6-difluoro-phenyl isothiocyanate, 2,6-dimethyl-phenyl isothiocyanate, 2-ethyl phenyl isothiocyanate, 2-chloro-4-nitro-phenyl isothiocyanate, 3-methoxy phenyl isothiocyanate, 4-(bromomethyl) phenyl isothiocyanate, 4-ethyl phenyl isothiocyanate, 5-chloro-2-methyl phenyl isothiocyanate, 1,4-dithio isocyanate-butane, 2-chloro-5-(trifluoromethyl) phenyl isothiocyanate, 2-methoxy-4-nitrophenyl isothiocyanate, 3,4,5-trimethoxy phenyl isothiocyanate, 3-(trifluoromethylthio) phenyl isothiocyanate, 4-chloro-3-(trifluoromethyl) phenyl isothiocyanate, 4-methyl-3-(trifluoromethyl) phenyl isothiocyanate, 2,3-dichloro-phenyl isothiocyanate, 2,4-dichloro-phenyl isothiocyanate, 2,5-dichloro phenyl isothiocyanate, 2,6-dichlorophenyl isothiocyanate, 2-(4-chlorophenyl) ethyl isothiocyanate, 2-(ethoxycarbonyl) phenyl isothiocyanate, 2-methoxy-5-methyl-phenyl isothiocyanate, 2-methoxy-phenyl thioisocyanate, 2-methoxy ethyl thioisocyanate, 3,4-dichloro-phenyl isothiocyanate, 3,5-dichloro-phenyl isothiocyanate, 4-fluoro-3-(trifluoromethyl) phenyl isothiocyanate, 4-iodophenyl isothiocyanate, 3-isothiocyanato tert-butyl benzoate, 4-isothiocyanato tert-butyl benzoate, diphenyl ethyl isothiocyanate.

Preferably, the isothiocyanates are selected from the following group: isothiocyanates, adducts of isothiocyanate and N-acetyl cysteine, or combinations thereof wherein the isothiocyanate is selected from the group: phenethyl isothiocyanate, allyl isothiocyanate, benzyl isothiocyanate, phenyl isothiocyanate, L-ethyl phenyl isothiocyanate, cyclohexyl isothiocyanate, 4-methoxy benzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanates, sulforaphane, or combinations thereof.

In another preferred embodiment, the first active ingredient is selected from the following group: phenethyl isothiocyanate, allyl isothiocyanate, benzyl isothiocyanate, phenyl isothiocyanate, L-ethyl phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-hexyl benzene isothiocyanate, trityl isothiocyanate, phenethyl isothiocyanate-N-acetyl cysteine adducts, sulforaphane, or combinations thereof.

In another preferred embodiment, the first active ingredient compound is derived from: animals and plants, chemical synthesis, or semi-chemical synthesis.

In another preferred embodiment, the second active ingredient is DNA-effecting or influencing anticancer drugs, kinase-inhibiting anticancer drugs or hormonal anticancer drug for endocrine therapy.

In another preferred embodiment, the DNA-effecting or influencing anticancer drug is one or more selected from the following group: alkylating agent anticancer drugs, DNA-damaging metal compound anticancer drugs, DNA intercalating agents or DNA-damaging antibiotics anticancer drugs, anticancer drugs that inhibit topoisomerase so as to inhibit the repair of DNA, anticancer drugs that inhibit DNA polymerase, anticancer drugs that affect tubulin so as to inhibit mitosis;

In another preferred embodiment, the alkylating agent anticancer drugs include: bendamustine, cyclophosphamide, lomustine, dacarbazine, temozolomide, thiotepa, carmustine, streptozocin, butopirane, busulfan.

In another preferred embodiment, the DNA-damaging metal compound anticancer drugs include: cisplatin, carboplatin, oxaliplatin, oxaliplatin, Schiff base metal complexes, organic tin metal complexes.

In another preferred embodiment, the DNA intercalating agent or antibiotics anticancer drugs damaging DNA include: bleomycin, doxorubicin, daunorubicin, epirubicin, mitoxantrone, aclacinomycin, actinomycin D, and mitomycin.

In another preferred embodiment, the anticancer drugs that inhibit topoisomerase so as to inhibit the repair of DNA include: topotecan, irinotecan, hydroxyl camptothecin.

In another preferred embodiment, the anticancer drugs that inhibit DNA polymerase include: cytarabine, fludarabine, gemcitabine.

In another preferred embodiment, anticancer drugs that affect tubulin so as to inhibit mitosis include: cabazitaxel, docetaxel (also known as docetaxel), paclitaxel, vincristine sulfate, vinblastine sulfate.

In another preferred embodiment, the DNA-effecting or influencing anticancer drug is one or more selected from the following group: Bendamustine, cyclophosphamide, lomustine, dacarbazine, temozolomide, carmustine, streptozocin, thiotepa, butoxy piperazine, busulfan, cisplatin, carboplatin, oxaliplatin, oxalic acid, Schiff base metal complexes, organic tin metal complex, bleomycin, doxorubicin, daunorubicin, epirubicin, mitoxantrone, adriamycin Accra, actinomycin D, mitomycin, topotecan, irinotecan, hydroxyl camptothecin, cytarabine, fludarabine, gemcitabine, Nelarabine, cabazitaxel, docetaxel, paclitaxel, vincristine sulfate, vinblastine sulfate.

In another preferred embodiment, the DNA-effecting or influencing anticancer drug is one or more selected from the following group: Bendamustine, cyclophosphamide, lomustine, dacarbazine, temozolomide, cisplatin, carboplatin, oxaliplatin, bleomycin, doxorubicin, daunorubicin, epirubicin, mitomycin, topotecan, fludarabine, gemcitabine, Nelarabine, cabazitaxel, docetaxel, paclitaxel, vincristine sulfate, vinblastine sulfate.

In another preferred embodiment, the kinase-inhibiting anticancer drug is one or more selected from the following group: receptor tyrosine kinase inhibitors, non-receptor tyrosine kinase inhibitors, multi-target kinase inhibitors, serine/threonine protein kinase inhibitor, Phosphoinositide 3-kinase inhibitor, rapamycin (PI3K-AKTmTOR) signaling pathway inhibitors, matrix metalloproteinase inhibitors, cell cycle-dependent protein kinase inhibitors, histone deacetylase (HDAC) inhibitor, 26S protease inhibitors, arsenic trioxide.

In another preferred embodiment, the receptor tyrosine kinase inhibitor includes: Gefitinib, erlotinib, lapatinib, Crizotinib.

In another preferred embodiment, the multi-target kinase inhibitor include: Axitinib, imatinib, sorafenib, vandetanib, sunitinib, pazopanib, stymzr, cediranib, Dovitinib, motesanib, Midostaurin.

In another preferred embodiment, the non-receptor tyrosine kinase inhibitor include: Bosutinib, nilotinib, dasatinib.

In another preferred embodiment, the serine/threonine protein kinase inhibitor includes: Vemurafenib, Hesperadin, MK0457, ZM447439, Wherein the structure of Hesperadin is

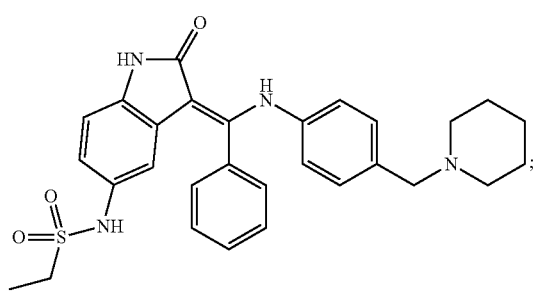 [SMILES: CCS(=O)(=O)Nc1ccc2c(c1)/C(=C(/Nc1ccc(CN3CCCCC3)cc1)c1ccccc1)C(=O)N2]

The structure of MK0457 is

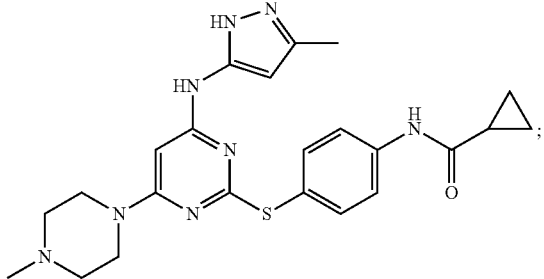 [SMILES: Cc1cc(Nc2cc(N3CCN(C)CC3)nc(Sc3ccc(NC(=O)C4CC4)cc3)n2)[nH]n1]

the structure of ZM447439 is

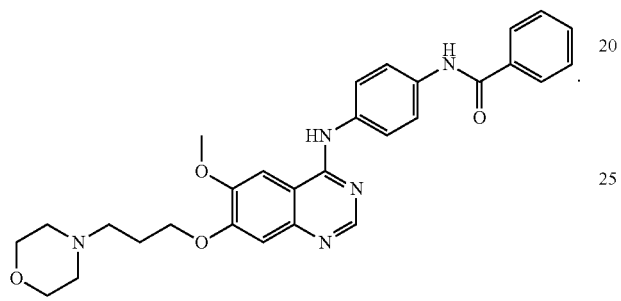

In another preferred embodiment, the Phosphoinositide 3-kinase inhibitor includes: wortmannin, quercetin derivatives.

In another preferred embodiment, the rapamycin (PI3K-AKTmTOR) signaling pathway inhibitor includes: everolimus, sirolimus.

In another preferred embodiment, the histone deacetylase inhibitor includes: romidepsin, vorinostat.

In another preferred embodiment, the 26S protease inhibitor includes: bortezomib.

In another preferred embodiment, the matrix metalloproteinase inhibitor includes: Batimastat, Tanomastat, marimastat, prinomastat.

In another preferred embodiment, the cell cycle-dependent protein kinase inhibitor includes: Flavopiridol, Staurosporine, Roscovitine, indirubin derivative;

wherein the CAS number of Flavopiridol is 146426-40-6, and the structure thereof is:

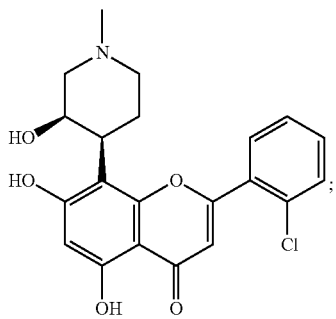 [SMILES: CN1CC[C@@H](c2c(O)cc(O)c3c(=O)cc(-c4ccccc4Cl)oc23)[C@@H](O)C1]

The CAS number of Staurosporine is 62996-74-1, and the structure thereof is:

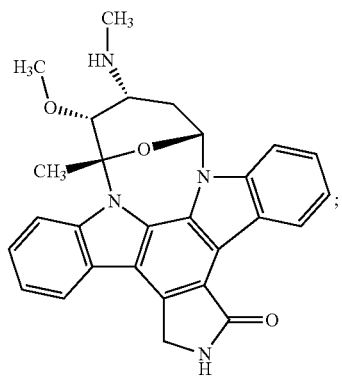 [SMILES: CN[C@@H]1C[C@H]2O[C@@](C)([C@@H]1OC)n1c3ccccc3c3c4c(c5c6ccccc6n2c5c31)C(=O)NC4]

the CAS number of Roscovitine is 186692-46-6, and the structure thereof is:

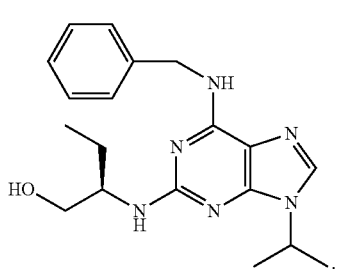 [SMILES: CC[C@H](CO)Nc1nc(NCc2ccccc2)c2ncn(C(C)C)c2n1]

In another preferred embodiment, the kinase-inhibiting anticancer drug is one or more selected from the following group: Axitinib, erlotinib, imatinib, nilotinib, pazopanib, sorafenib, Bosutinib, dasatinib, gefitinib, lapatinib, sunitinib, vandetanib, stymzr, cediranib, Dovitinib, motesanib, Midostaurin, Vemurafenib, Hesperadin, MK0457, ZM447439, everolimus, sirolimus, romidepsin, vorinostat, arsenic trioxide, bortezomib, Warman penicillin, Flavopiridol, Staurosporine, Roscovitine, quercetin derivatives, indirubin derivatives.

In another preferred embodiment, the kinase-inhibiting anticancer drug is one or more selected from the following group: Axitinib, erlotinib, imatinib, nilotinib, pazopanib, sorafenib, everolimus, arsenic trioxide, bortezomib, romidepsin, vorinostat, Vemurafenib.

In another preferred embodiment, the hormonal anticancer drug for endocrine therapy is one or more selected from the following group: Gonadotropin drugs, anti-androgen drugs, anti-secretion of adrenal and cortical hormone drugs, estrogen and progesterone drugs, 5α-reductase inhibitors, androgen receptor signaling inhibitor, CYP450c17 inhibitors.

In another preferred embodiment, the hormonal anticancer drug for endocrine therapy is one or more selected from the following group: LHRH analogues, LHRH antagonists, anti-androgen drugs, CYP450c17 inhibitors, androgen receptor signaling inhibitor.

In another preferred embodiment, the LHRH analogue includes Leuprolide, goserelin, buserelin, triptorelin.

In another preferred embodiment, the LHRH antagonist includes Cetrorelix, Abarelix.

In another preferred embodiment, the anti-androgen drug includes Bicalutamide, flutamide, nilutamide.

In another preferred embodiment, the estrogen and progesterone drug includes diethylstilbestrol, cyproterone, megestrol.

In another preferred embodiment, the androgen receptor signaling inhibitor includes Enzalutamide.

In another preferred embodiment, the CYP450c17 inhibitor includes abiraterone.

In another preferred embodiment, the anti-secretion of adrenal and cortical hormone drug includes Ketoconazole, aminoglutethimide, prednisone, prednisolone.

In another preferred embodiment, the hormonal anticancer drug for endocrine therapy is one or more selected from the following group: Leuprolide, goserelin, Bicalutamide, flutamide, Enzalutamide, prednisolone, abiraterone, or pharmaceutically acceptable deriviatives or analogues thereof.

In another preferred embodiment, the hormonal anticancer drug for endocrine therapy is one or more selected from the following group: Leuprolide, goserelin, Bicalutamide, flutamide, Enzalutamide, abiraterone.

In another preferred embodiment, the weight ratio of the first active ingredient to the second active ingredient is 1:10000 to 10000:1; preferrably is 1:1000 to 1000:1; more preferably is 1:500 to 500:1; more preferably is 1:100 to 100:1; more preferably is 10:90 to 100:1.

In another preferred embodiment, the composition is used in the preparation of drugs, health products or foods for inhibiting cancer cells, or in the preparation of anti-cancer drugs.

In the second aspect of the present invention, a kit is provided, wherein the kit comprises:

(A) a first formulation comprising isothiocyanates or derivatives thereof;

(B) a second formulation comprising DNA-effecting or influencing anticancer drugs, kinase-inhibiting anticancer drugs or hormonal anticancer drugs for endocrine therapy;

(C) instructions for use.

In another preferred embodiment, the isothiocyanate is a compound of formula (I) or a derivative of compound (II):

In another preferred embodiment, the isothiocyanate or derivatives thereof is selected from the following group: phenethyl isothiocyanate, allyl isothiocyanate, benzyl isothiocyanate, phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanate, sulforaphane, phenethyl isothiocyanate-N-acetyl cysteine adduct, or combinations thereof.

In another preferred embodiment, the DNA-effecting or influencing anticancer drug is one or more selected from the following group: alkylating agent anticancer drugs, DNA-damaging metal compound anticancer drugs, DNA intercalating agents or DNA-damaging antibiotics anticancer drugs, anticancer drugs that inhibit topoisomerase so as to inhibit the repair of DNA, anticancer drugs that inhibit DNA polymerase, anticancer drugs that affect tubulin so as to inhibit mitosis.

In another preferred embodiment, the DNA-effecting or influencing anticancer drug is one or more selected from the following group: Bendamustine, cyclophosphamide, lomustine, dacarbazine, temozolomide, carmustine, streptozocin, thiotepa, butoxy piperazine, busulfan, cisplatin, carboplatin, oxaliplatin, oxalic acid, Schiff base metal complexes, organic tin metal complex, bleomycin, doxorubicin, daunorubicin, epirubicin, mitoxantrone, adriamycin Accra, actinomycin D, mitomycin, topotecan, irinotecan, hydroxyl camptothecin, cytarabine, fludarabine, gemcitabine, Nelarabine, cabazitaxel, docetaxel, paclitaxel, vincristine sulfate, vinblastine sulfate.

In another preferred embodiment, the kinase-inhibiting anticancer drug is one or more selected from the following group: receptor tyrosine kinase inhibitors, non-receptor tyrosine kinase inhibitors, multi-target kinase inhibitors, serine/threonine protein kinase inhibitor, Phosphoinositide 3-kinase inhibitor, rapamycin (PI3K-AKTmTOR) signaling pathway inhibitors, matrix metalloproteinase inhibitors, cell cycle-dependent protein kinase inhibitors, histone deacetylase (HDAC) inhibitor, 26S protease inhibitors, arsenic trioxide.

In another preferred embodiment, the kinase-inhibiting anticancer drug is one or more selected from the following group: Axitinib, erlotinib, imatinib, nilotinib, pazopanib, sorafenib, Bosutinib, dasatinib, gefitinib, lapatinib, sunitinib, vandetanib, stymzr, cediranib, Dovitinib, motesanib, Midostaurin, Vemurafenib, Hesperadin, MK0457, ZM447439, everolimus, sirolimus, romidepsin, vorinostat, arsenic trioxide, bortezomib, Warman penicillin, Flavopiridol, Staurosporine, Roscovitine, quercetin derivatives, indirubin derivatives.

In another preferred embodiment, the hormonal anticancer drug for endocrine therapy is one or more selected from the following group: LHRH analogues, LHRH antagonists, anti-androgen drugs, CYP450c17 inhibitors, androgen receptor signaling inhibitor.

In another preferred embodiment, the hormonal anticancer drug for endocrine therapy is one or more selected from the following group: Leuprolide, goserelin, Bicalutamide, flutamide, Enzalutamide, abiraterone.

In another preferred embodiment, the instructions for use indicate that the first formulation and the second formulation are used in combination to inhibit the growth of tumor cells or treat cancer.

In another preferred embodiment, the first formulation and the second formulation are used simultaneously, separately or in sequence in inhibiting the growth of tumor cells or treating cancer.

In the third aspect of the present invention, a combination of active ingredients is provided, wherein the combination comprises the following ingredients, or is formed by combining the following ingredients:

(A) a first active ingredient, wherein the first active ingredient is isothiocyanates or derivatives thereof;

(B) a second active ingredient, wherein the second active ingredient is DNA-effecting or influencing anticancer drugs, kinase-inhibiting anticancer drugs, or hormonal anticancer drugs for endocrine therapy.

In another preferred embodiment, in the combination, the weight ratio of the first active ingredient to the second active ingredient is 1:10000 to 10000:1.

In another preferred embodiment, the composition is used in the preparation of drugs, health products or foods for inhibiting cancer cells, or in the preparation of anti-cancer drugs.

In the fourth aspect of the present invention, a use of the composition of the first aspect of the present invention or the combination of the third aspect of the present invention is provided, in the preparation of drugs, health products or foods for inhibiting cancer cells, or in the preparation of anti-cancer drugs.

In another preferred embodiment, the cancer is selected from: bone cancer, stomach cancer, cervical cancer, brain cancer, liver cancer, prostate cancer, lung cancer, breast cancer, colon colorectal cancer, colon cancer, kidney cancer, bladder cancer, pancreatic cancer, endometrial cancer, ovarian cancer, skin cancer, leukemia, non-Hodgkin's lymphoma, lymphoma or malignant melanoma.

In another preferred embodiment, the prostate cancer includes androgen-independent prostate cancer and androgen-dependent prostate cancer.

In another preferred embodiment, the cancer cell includes human osteocarcinoma Saos-2 cells, human gastric cancer AGS cells, human ovarian cancer OVCAR-3 cells, human cervical cancer HeLa cells, human leukemia HL-60 cells, human lung cancer A549 cells, human pancreatic cancer PANC-1 cells, human brain cancer U251 cells, human lymphoma Jurkat E6-1 cells, malignant melanoma SK-MEL-28 cells, human prostate carcinoma DU145 cells, human breast cancer MDA-MB-231 cells, human prostate cancer PC-3 cells, human prostate cancer LNCaP cells, human kidney cancer 786-0 cells, human colon cancer HT29 cells.

In another preferred embodiment, before, simultaneous with or after using the composition or pharmaceutical composition, other active ingredients for treating cancer are coordinately used, surgery against cancer is conducted or radiation therapy against cancer is adminstered, or gene therapy is used in combination, or bio-regulators are used in combination.

In another preferred embodiment, other cancer treating active ingredients are etoposide, 5-fluorouracil.

In the fifth aspect of the present invention, a pharmaceutical composition for treating cancer is provided, wherein the pharmaceutical composition comprises:

(A) therapeutically effective amount of a first active ingredient, wherein the first active ingredient is isothiocyanates or derivatives thereof;

(B) therapeutically effective amount of a second active ingredient, wherein the second active ingredient is DNA-effecting or influencing anticancer drugs, kinase-inhibiting anticancer drugs or hormonal anticancer drugs for endocrine therapy;

(C) pharmaceutically acceptable carriers, and the weight ratio of the first active ingredient to the second active ingredient is 1:10000 to 10000:1.

In the sixth aspect of the present invention, an in vitro non-therapeutic method of inhibiting the growth of cancer cells is provided, which comprises the following steps: using the composition of the first aspect of the present invention, the combination of active ingredients of the third aspect of the present invention or the pharmaceutical composition of the fifth aspect of the present invention to inhibit the growth of cancer cells.

In another preferred embodiment, the method comprises the step: culturing cancer cells in the presence of the first active ingredient, the second active ingredient and the cancer cells, thereby inhibiting the growth of the cancer cells.

In another preferred embodiment, the method comprises the following steps:

(1) culturing cancer cells for 20-30 hours;

(2) adding the first active ingredient and the second active ingredient, and then culturing for another 1-100 hours;

(3) determining the cell viability and calculating the combination index CI value.

In the seventh aspect of the present invention, a method for treating or preventing cancer is provided, which comprises the following steps: administering the composition of the first aspect of the present invention, the combination of active ingredients of the third aspect of the present invention or the pharmaceutical composition of the fifth aspect of the present invention to a subject in need thereof.

In another preferred embodiment, the cancer is bone cancer, stomach cancer, cervical cancer, brain cancer, liver cancer, prostate cancer, lung cancer, breast cancer, colon colorectal cancer, colon cancer, kidney cancer, bladder cancer, pancreatic cancer, endometrial cancer, ovarian cancer, skin cancer, leukemia, non-Hodgkin's lymphoma, lymphoma or malignant melanoma.

In another preferred embodiment, the subject is a mammal (such as human).

In another preferred embodiment, the daily administering amount of the composition is 0.1 mg-2000 mg (preferably 1 mg-1500 mg).

In another preferred embodiment, the daily administering amount of the first active ingredient is 0.1 mg-1000 mg (preferably 1-500 mg), and the daily administering amount of the second active ingredient is 0.01 mg-1500 mg (preferably 0.1-1500 mg; more preferably 1 mg-1500 mg; more preferably 1 mg-500 mg).

Preferably, the administering amount is calculated by every kg of body weight.

In another preferred embodiment, the administration includes successively administering the first active ingredient and the second active ingredient, or simultaneously administering the first active ingredient and the second active ingredient.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After extensive and in-depth study, the present inventors have unexpectedly discovered that combining isothiocyanates or derivatives thereof and DNA-effecting or influencing anticancer drugs, kinase inhibiting anticancer drugs or hormonal anticancer drugs for endocrine therapy will have synergistic effects on cancer. Wherein combining the isothiocyanates or derivatives thereof and hormonal anticancer drugs for endocrine therapy can have synergistic effects on hormone-dependent prostate cancer and hormone-independent prostate cancer. The effect of synergistic treatment is better than that of using each of them alone. The present invention is completed on this basis.

The First Active Ingredient

The first active ingredient of the present invention is isothiocyanates or derivatives thereof, wherein the first active ingredient is a compound of formula (I) or derivatives of compound (II), or combinations thereof:

A-NCS  (formula I)

Wherein in the formula I,

NCS is isothiocyanate group;

A is $—XR_1$ or $—CR_2R_3R_4$; wherein

X is $—(CH_2)n-$, n is an integer of 0-6;

$R_1$ is a methyl, t-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, t-octyl, chlorine atom, trimethylsilyl, or substituted or unsubstituted phenyl;

Wherein "substituted" means that one or more Hs in a group are substituted by substituents selected from the following group: a halogen, methyl, bromomethyl, ethyl, methoxy, nitro, azido, trifluoromethyl, difluoromethoxy, methylthio, cyano, trifluoromethoxy, trifluoromethylthio, t-butoxycarbonyl, and ethoxy carbonyl;

$R_2$, $R_3$, $R_4$ are independently H, phenyl or $C_{1-3}$ alkyl;

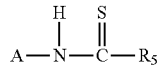

(formula II)

wherein in formula II:

A is defined as in formula I;

$R_5$ is a hydrogen, or a group derived from the following compounds, wherein the group is connected to the carbon atom of

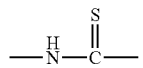

via sulphur atom: N-acetylcysteine, glutathione, cysteine ($C_{1-6}$ alkyl) ester, cysteinyl amino acid and cysteinyl amino acid ($C_{1-6}$ alkyl) ester.

In another preferred embodiment, the amino acid is selected from: glycine, glutamic acid, serine, alanine, or methionine.

A type of preferred first active ingredient is selected from the following group: isothiocyanates, adducts of isothiocyanate and N-acetylcysteine, or combinations thereof;

wherein the isothiocyanates are selected from the following group: ethyl phenyl isothiocyanate, cyclohexyl isothiocyanate, 4-methoxybenzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanate, 1-isothiocyanate-4-methanesulfonyl butane (sulforaphane), isothiocyanate α-methyl benzyl ester, hexyl isothiocyanate, isothiocyanate methyl cyclohexyl ester, 1-naphthyl isothiocyanate, 2-chlorophenyl isothiocyanate, 2-bromophenyl isothiocyanate, 3-chlorophenyl isothiocyanate, 3-bromophenyl isothiocyanate, 3-nitrophenyl isothiocyanate, 4-azido phenyl isothiocyanate, 4-fluorophenyl isothiocyanate, 4-chlorophenyl isothiocyanate, 4-bromophenyl isothiocyanate, 4-nitrophenyl isothiocyanate, ethoxycarbonyl isothiocyanate, tert-octyl isothiocyanate, p-tolyl isothiocyanate, benzoyl isothiocyanate, o-tolyl isothiocyanate, m-tolyl isothiocyanate, 2,3,4-trifluorophenyl isothiocyanate, 2,5-dimethoxyphenyl isothiocyanate, 2-(4-morpholino) ethyl isothiocyanate, 2-(trifluoromethyl) phenyl isothiocyanate, 2-(difluoromethoxy) phenyl isothiocyanate, 2-(methylthio) phenyl isothiocyanate, 2-fluoro-5-(trifluoromethyl) phenyl isothiocyanate, 3,5-bis(trifluoromethyl) phenyl isothiocyanate, 3-(4-morpholino) propyl isothiocyanate, 3-(trifluoromethyl) phenyl isothiocyanate, 3-(diethylamino) propyl isothiocyanate, 3-(methylthio) propyl isothiocyanate, 3-(methylthio) phenyl isothiocyanate, 3-cyano-phenyl isothiocyanate, 4-(trifluoromethyl) phenyl isothiocyanate, 4-(trifluoromethoxy) phenyl isothiocyanate, 4-(trifluoromethylthio) phenyl isothiocyanate, 4-(difluoromethoxy) phenyl isothiocyanate, 4-(methylthio) phenyl isothiocyanate, 4-cyano phenyl isothiocyanate, 4-bromo-2-fluorophenyl isothiocyanate, 4-methoxy-phenyl isothiocyanate, methallyl isothiocyanate, 2-(4-isothiocyanato-phenoxy) toluenesulfonate ethyl ester, 2-chloro-ethyl isothiocyanate, (2-fluorophenyl) isothiocyanate, (3-fluorophenyl) isothiocyanate, butyl isothiocyanate, trimethylsilyl isothiocyanate, propyl isothiocyanate, ethyl isothiocyanate, tert-butyl isothiocyanate, isopropyl isothiocyanate, allyl isothiocyanate, methyl isothiocyanate, phenethyl isothiocyanate, benzyl isothiocyanate, phenyl isothiocyanate, 2,4,5-trichloro phenyl isothiocyanate, 2,4,6-trichloro-phenyl isothiocyanate, 2,4-difluoro-phenyl isothiocyanate, 2,5-difluoro-phenyl isothiocyanate, 2,6-difluoro-phenyl isothiocyanate, 2,6-dimethyl-phenyl isothiocyanate, 2-ethyl phenyl isothiocyanate, 2-chloro-4-nitro-phenyl isothiocyanate, 3-methoxy phenyl isothiocyanate, 4-(bromomethyl) phenyl isothiocyanate, 4-ethyl phenyl isothiocyanate, 5-chloro-2-methyl phenyl isothiocyanate, 1,4-dithio isocyanate-butane, 2-chloro-5-(trifluoromethyl) phenyl isothiocyanate, 2-methoxy-4-nitro-phenyl isothiocyanate, 3,4,5-trimethoxy phenyl isothiocyanate, 3-(trifluoromethylthio) phenyl isothiocyanate, 4-chloro-3-(trifluoromethyl) phenyl isothiocyanate, 4-methyl-3-(trifluoromethyl) phenyl isothiocyanate, 2,3-dichloro-phenyl isothiocyanate, 2,4-dichloro-phenyl isothiocyanate, 2,5-dichloro phenyl isothiocyanate, 2,6-dichloro-phenyl isothiocyanate, 2-(4-chlorophenyl) ethyl isothiocyanate, 2-(ethoxycarbonyl) phenyl isothiocyanate, 2-methoxy-5-methyl-phenyl isothiocyanate, 2-methoxy-phenyl thioisocyanate, 2-methoxy ethyl thioisocyanate, 3,4-dichloro-phenyl isothiocyanate, 3,5-dichloro-phenyl isothiocyanate, 4-fluoro-3-(trifluoromethyl) phenyl isothiocyanate, 4-iodophenyl isothiocyanate, 3-isothiocyanato tert-butyl benzoate, 4-isothiocyanato tert-butyl benzoate, diphenyl ethyl isothiocyanate.

Preferably it is selected from the following group: isothiocyanates, adducts of isothiocyanate and N-acetylcysteine, or combinations thereof;

wherein the isothiocyanate is selected from the following group: phenethyl isothiocyanate, allyl isothiocyanate, benzyl isothiocyanate, phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanate, sulforaphane or combinations thereof.

In another preferred embodiment, the first active ingredient is selected from the following group: phenethyl isothiocyanate, allyl isothiocyanate, benzyl isothiocyanate, phenyl isothiocyanate, cyclohexyl isothiocyanate, 4-methoxy-benzyl isothiocyanate, 4-chloro-benzyl isothiocyanate, phenylpropyl isothiocyanate, 4-phenyl-butyl isothiocyanate, 6-phenyl-hexyl isothiocyanate, trityl isothiocyanate, phenethyl isothiocyanate-N-acetyl cysteine adduct, sulforaphane, or combinations thereof.

The isothiocyanates or derivatives thereof as said above can be used alone or in combinations of two or more of them. When used in combinations, the respective weight ratio of each compound is not particularly limited, as long as therapeutic purposes can be achieved.

In the present invention, there is no particular limitation on the method for obtaining isothiocyanates, for example, it can be extracted from natural plants (such as mustard or turnip), prepared by chemical synthesis or semi-chemical synthesis, etc. Isothiocyanates of the invention can be commercially available, for example from Sigma-Aldrich Company.

The Second Active Ingredient

The second active ingredient can be DNA-effecting or influencing anticancer drugs, wherein the DNA-effecting or influencing anticancer drug is one or more selected from the following group: alkylating agent anticancer drugs, DNA-damaging metal compound anticancer drugs, DNA intercalating agents or DNA-damaging antibiotics anticancer drugs, anticancer drugs that inhibit topoisomerase so as to inhibit the repair of DNA, anticancer drugs that inhibit DNA polymerase, anticancer drugs that affect tubulin so as to inhibit mitosis.

In another preferred embodiment, the DNA-effecting or influencing anticancer drug is one or more selected from the following group: Bendamustine, cyclophosphamide, lomustine, dacarbazine, temozolomide, carmustine, streptozocin, thiotepa, butoxy piperazine, busulfan, cisplatin, carboplatin, oxaliplatin, oxalic acid, Schiff base metal complexes, organic tin metal complex, bleomycin, doxorubicin, daunorubicin, epirubicin, mitoxantrone, adriamycin Accra, actinomycin D, mitomycin, topotecan, irinotecan, hydroxyl camptothecin, cytarabine, fludarabine, gemcitabine, Nelarabine, cabazitaxel, docetaxel, paclitaxel, vincristine sulfate, vinblastine sulfate.

In another preferred embodiment, the DNA-effecting or influencing anticancer drug is one or more selected from the following group: Bendamustine, cyclophosphamide, lomustine, dacarbazine, temozolomide, cisplatin, carboplatin, oxaliplatin, bleomycin, doxorubicin, daunorubicin, epirubicin, mitomycin, topotecan, fludarabine, gemcitabine, Nelarabine, cabazitaxel, docetaxel, paclitaxel, vincristine sulfate, vinblastine sulfate.

The second active ingredient can be a kinase-inhibiting anticancer drugs, and the kinase inhibiting anticancer drug is one or more selected from the following group: receptor tyrosine kinase inhibitors, non-receptor tyrosine kinase inhibitors, multi-target kinase inhibitors, serine/threonine protein kinase inhibitor, Phosphoinositide 3-kinase inhibitor, rapamycin (PI3K-AKTmTOR) signaling pathway inhibitors, matrix metalloproteinase inhibitors, cell cycle-dependent protein kinase inhibitors, histone deacetylase (HDAC) inhibitor, 26S protease inhibitors, arsenic trioxide.

In another preferred embodiment, the kinase-inhibiting anticancer drug is one or more selected from the following group: Axitinib, erlotinib, imatinib, nilotinib, pazopanib, sorafenib, Bosutinib, dasatinib, gefitinib, lapatinib, sunitinib, vandetanib, stymzr, cediranib, Dovitinib, motesanib, Midostaurin, Vemurafenib, Hesperadin, MK0457, ZM447439, everolimus, sirolimus, romidepsin, vorinostat, arsenic trioxide, bortezomib, Warman penicillin, quercetin derivatives, Flavopiridol, Staurosporine, Roscovitine, indirubin derivatives.

In another preferred embodiment, the kinase-inhibiting anticancer drug is one or more selected from the following group: Axitinib, erlotinib, imatinib, nilotinib, pazopanib, sorafenib, everolimus, arsenic trioxide, bortezomib, romidepsin, vorinostat, Vemurafenib.

The second active ingredient can be hormonal anticancer drugs for endocrine therapy, and the hormonal anticancer drug for endocrine therapy is one or more selected from the following group: Gonadotropin drugs, anti-androgen drugs, anti-secretion of adrenal and cortical hormone drugs, estrogen and progesterone drugs, 5α-reductase inhibitors, androgen receptor signaling inhibitor, CYP450c17 inhibitors.

In another preferred embodiment, the hormonal anticancer drug for endocrine therapy is one or more selected from the following group: LHRH analogues, LHRH antagonists, anti-androgen drugs, CYP450c17 inhibitors, androgen receptor signaling inhibitor.

In another preferred embodiment, the LHRH analogue includes Leuprolide, goserelin, buserelin, triptorelin.

In another preferred embodiment, the LHRH antagonist includes Cetrorelix, Abarelix.

In another preferred embodiment, the anti-androgen drug includes Bicalutamide, flutamide, nilutamide.

In another preferred embodiment, the estrogen and progesterone drug includes diethylstilbestrol, cyproterone, megestrol.

In another preferred embodiment, the androgen receptor signaling inhibitor includes Enzalutamide.

In another preferred embodiment, the CYP450c17 inhibitor includes abiraterone.

In another preferred embodiment, the anti-secretion of adrenal and cortical hormone drug includes Ketoconazole, aminoglutethimide, prednisone, prednisolone.

In another preferred embodiment, the hormonal anticancer drug for endocrine therapy is one or more selected from the following group: Leuprolide, goserelin, Bicalutamide, Enzalutamide, abiraterone, prednisolone, or the pharmaceutically acceptable deriviatives, metabolites, or analogues thereof.

In another preferred embodiment, the hormonal anticancer drug for endocrine therapy is one or more selected from the following group: Leuprolide, goserelin, Bicalutamide, flutamide, Enzalutamide, abiraterone.

Compositions, Kits, Combinations of Active Ingredients and Pharmaceutical Compositions The composition of the present invention can be pharmaceutical compositions (drugs), food or health products, said composition comprising:

(A) therapeutically effective amount of a first active ingredient;

(A) therapeutically effective amount of a second active ingredient;

and the weight ratio of the first active ingredient to the second active ingredient is 1:10000 to 10000:1, preferably 1:1000 to 1000:1.

In the pharmaceutical composition of the present invention, the content of the first active ingredient is in a range of 0.01 to 99.99%, based on the total weight of the composition; preferably 0.1% to 99.9%, and more preferably 20% to 99%. The content of the second active ingredient is in a range of 0.01 to 99.99%, based on the total weight of the composition, preferably 1% to 99%, and more preferably 1% to 90%.

If necessary, the composition may also comprise acceptable carriers to pharmaceutics, bromatology, and health products. As used herein, the term ingredients "acceptable to pharmaceutics, bromatology, and health products" means substances suitable for applying to humans and/or animals without undue undesired side-reactions (such as toxicity, stimulation or allergy), that is, with reasonable benefit/risk ratio. As used herein, the term "effective amount" means an amount which may exert function or activity to human and/or animals and be acceptable for human and/or animal.

As used herein, the term "pharmaceutically acceptable carrier" means carriers for delivery of therapeutic agents, including a variety of excipients and diluents. This term refers to such pharmaceutical carrier which themselves are not essential active components and without undue toxic after administration. Suitable carriers are well-known to those of ordinary skill in the art.

The pharmaceutics, food, health product compositions comprising the first active ingredient, the second active ingredient, or derivatives, metabolites therefore according to the present invention may be in various dosage forms suitable for oral administration, and may also be various topical formulations or other kinds of parenteral preparations. For example, the topical administration formulations of the present invention may also be further prepared into (including but not limited to): liniments, tinctures, oils, ointments, plasters, pastes, ironing agents, plaster, patch, plastics, films, gels, cataplasms, acupoint application formulations, sprays, aerosols, implants, emulsions and the like, by adding surfactants, penetration enhancers, preservatives, solvents, antioxidants, humectants, pH adjusting agents, colorants, perfumes and other auxiliary materials. For cancer, the preferred dosage forms include: various dosage forms for oral administration, implants, injections.

The auxiliary materials added in the compositions of the present invention are commonly used auxiliary materials in the art, types, method for use and source of which are well-known to those skilled in the art.

The present invention also provided a combination of active ingredients, wherein the combination comprises the following ingredients, or is formed by combining the following ingredients:

(A) a first active ingredient, wherein the first active ingredient is isothiocyanates or derivatives thereof;

(B) a second active ingredient, wherein the second active ingredient is DNA-effecting or influencing anticancer drugs, kinase-inhibiting anticancer drugs, or hormonal anticancer drugs for endocrine therapy.

In the combination, the weight ratio of the first active ingredient to the second active ingredient is 1:10000 to 10000:1.

The present invention also provided a kit, wherein the kit comprises:

(A) a first preparation comprising therapeutically effective amount of isothiocyanates or derivatives thereof;

(B) a second preparation comprising DNA-effecting or influencing anticancer drugs, kinase-inhibiting anticancer drugs or hormonal anticancer drugs for endocrine therapy;

(C) instructions for use.

The instructions for use indicate that the first formulation and the second formulation are used in combination to inhibit the growth of tumor cells or treat cancer.

The composition, combination of active ingredients, pharmaceutical composition, kit, food and health product of the present invention can be prepared by conventional methods and equipments.

Use and Administration Mode of Compositions, Combinations of Active Ingredients, Pharmaceutical Compositions, and Kits The present invention provides the use of the above composition, the active ingredient combination, the pharmaceutical composition in preparing cancer cells inhibiting drugs, health products or foods, or in preparing anti-cancer drugs, health products or foods, or preparing anti-cancer medicaments.

The composition, kit, combination of active ingredients and pharmaceutical composition provided in the present invention can exert synergistic effect on the inhibition of cancer cells such as bone cancer, stomach cancer, cervical cancer, brain cancer, liver cancer, prostate cancer, breast cancer, lung cancer, colorectal cancer, bladder cancer, pancreatic cancer, endometrial cancer, ovarian cancer, skin cancer, leukemia, non-Hodgkin's lymphoma. Not limiting to theory, the mechanism of the composition, kit, combination of active ingredients and pharmaceutical composition according to the present invention in inhibiting growth and metastasis of cancer cells is likely of multi-level and multi-target. Cancer cells are inhibited by them through several different mechanisms and pathways. For example, it can restore the expression of poison clearing gene glutathione-S transferase P1 (GSTP1), induce cell cycle arrest, and induce apoptosis. While the induction of cell cycle arrest is completed in several pathways: inducing cell cycle arrest protein Cdk1 and degrading cell division cycle protein Cdc25C. The inductions of apoptosis is achieved through mediating Bax and Bak proteins, reducing the expression of apoptosis inhibitor protein XIAP and Survivin, and inhibiting oxidative phosphorylation from inducing the reactive oxygen activity, as well as promoting the P53 expression and activating AP-1, and so on.

Before, simultaneously with to or after using the composition, combination of active ingredient, pharmaceutical composition and kit of the present invention, other active ingredients for treating cancer (such as Etoposide, 5-Fluorouracil, etc.) are coordinately used, surgery against cancer is conducted or radiation therapy against cancer is adminstered, or gene therapy is used in combination, or bioregulators are used in combination.

When the first formulation and second formulation in the kit of the invention are used in combination, the first formulation and second formulations can be administered simultaneously, separately or sequentially. The safe and effective daily dosage of the active ingredient in the first formulation typically is 0.1 mg-2000 mg, preferably 1 mg-500 mg, more preferably 1 mg-300 mg, while the safe and effective daily dose of the active ingredient in the second formulation is generally 0.01 mg-1500 mg, preferably 0.1-1500 mg, more preferably 1 mg-1500 mg, more preferably 1 mg-500 mg. Administration modes include: when administered in combination, the first formulation can be administered orally, topically or by other parenteral routes, and the second formulation can be administered orally, topically or by other parenteral routes.

During the combined medication, the interaction between drugs, according to the effect of drugs when used together, can be sorted into adductive effect, synergy effect, antagonism effect, wherein synergy effect refers to that the effect of the drugs when used together is many times greater than that when used alone, adductive effect refers to that the effect of the drugs when used together equals to that when used alone, and antagonism effect refers to that the effect of the drugs when used together is inferior to that when used alone. In the present invention, it was firstly found that the first formula and the second formula have synergy effect.

A method for treating or preventing cancer is also provided in the present invention, which comprises the following steps: administering the composition, combination of active ingredients, pharmaceutical composition or kit of the present invention to a subject in need thereof, wherein the daily administration dose of the active ingredient is 1 mg to 10 mg. The subject is a mammal, preferably human.

In the inhibition of cancer cells or prevention or treatment of cancer, the administration mode of the present invention comprises successively administering the first active ingredient and the second active ingredient, or simultaneously administering the first active ingredient and the second active ingredient.

When using the composition, combination of active ingredients, pharmaceutical composition of the present invention, safe and effective amount of the composition, combination of active ingredients, pharmaceutical composition of the present invention is administered to a mammal, wherein the safe and effective daily amount of the first active ingredient is typically at least 0.1 mg, and in most cases, less than 2000 mg. Preferably, the amount is 1 mg-500 mg. The safe and effective amount of the second active ingredient is typically at least about 0.01 mg, and in most cases, less than 1500 mg. Preferably, the amount is 0.1 mg to 1500 mg. (Wherein, the safe and effective amount of the first active ingredient will usually less than about 2000 mg/kg of body weight. Preferably, the amount is about 100 μg/kg of body weight to about 1000 mg/kg of body weight; the safe and effective amount of the second active ingredient is usually less than about 2000 mg/kg of body weight. Preferably, the amount is about 10 μg/kg of body weight to about 1000 mg/kg of body weight). Of course, the particular dose should also depend on various factors, such as the route of administration, healthy status of a patient, which are all well within the skills of an experienced physician. There is no specific requirement on the interval of administration when successively administering the first active ingredient and the second active ingredient. The first and second active ingredient in the composition, combination of active ingredients, pharmaceutical composition and kit of the present invention can be administered simultaneously or successively via the same or different routes, which includes but not limited to: oral administration, injection administration, intratumoral administration, implantation administration, intracavitary administration, rectal administration, transdermal administration, internal and external application;

Preferable injection administration includes: intravenous, intramuscular, subcutaneous, intraarticular injection.

A non-treatment in vitro method for inhibiting the growth of cancer cells is also provided in the present invention, wherein the method comprises the step of using the composition, combination of active ingredients, pharmaceutical composition and kit of the present invention to inhibit the growth of cancer cells, that is, culturing cancer cells in the presence of the first active ingredient, the second active ingredient and cancer cells, thereby inhibiting the growth of the cancer cells.

Specifically, the method comprises the following steps:
(1) culturing cancer cells for 20-30 hours;
(2) adding the first active ingredient and the second active ingredient, and then culturing for another 1-100 hours; and
(3) determining the cell viability and calculating the combination index CI value.

Compared with the prior art, the main advantages of the composition, combination of active ingredients, pharmaceutical composition and kit of the present invention are:
(1) it is confirmed in the present invention by using cell biology method that isothiocyanates or derivatives thereof can effectively inhibit the growth of cancer cells.
(2) in the present invention, it is discovered that using isothiocyanates or derivatives thereof in combination of DNA-effecting or influencing anticancer drugs, kinase-inhibiting anticancer drugs or hormonal anticancer drugs for endocrine therapy can synergistically act on cancer cells, thereby improving the therapeutic effects on cancer. Meanwhile, the dose of DNA-effecting or influencing anticancer drugs, kinase-inhibiting anticancer drugs or hormonal anticancer drugs for endocrine therapy can be effectively reduced for achieving the same therapeutic effect, side effects of treatment can be reduced and the quality of life of patients can be improved, thereby providing a new class of drugs for the prevention and treatment of cancer.
(3) the present invention can effectively slow down and delay the occurrence of cancer, prolong the lives of patients and reduce mortality.

The technical features described above or in the Examples can be arbitrary combined. All of the features disclosed in the specification in this case may be used in any combination, various features disclosed in the specification can optionally be replaced by the same, equal or similar alternative features. Therefore, unless otherwise stated, the disclosed features are only general examples of equal or similar features.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Unless otherwise defined, the technical terms and scientific terminology used herein are of the same meanings as with that familiar to all to those skilled in the art. In addition, any methods and materials similar or equal to that recorded can be applied in the method described in the present invention. The preferred embodiments and the materials described herein are for demonstration purposes only.

Test I. General Experimental Materials and Methods

Phenethyl isothiocyanate, cyclohexyl isothiocyanate, sulforaphane, trityl isothiocyanate, phenethyl isothiocyanate-N-acetylcysteine adduct (PEITC-NAC), 4-phenylbutyl isothiocyanate (PITC), 6-phenethyl isothiocyanate (PITC), 3-phenylpropyl ITC, 4-chlorobenzyl isothiocyanate, L-ethyl phenyl isothiocyanate (L-alpha-methylbenzyl), benzyl isothiocyanate (BITC), 4-methoxy-benzyl isothiocyanate; Bleomycin, Bendamustine, Cisplatin, Cyclophosphamide, Carboplatin, Doxorubicin, Dacarbazine, Topotecan, Fludarabine, Gemcitabine, Lomustine, Nelarabine, Daunorubicin, Cabazitaxel, docetaxel, paclitaxel, vincristine sulfate, vinblastine sulfate, methotrexate.

Cell culture: HeLa cell, Jurkat E6-1 cell, OVCAR-3 cell, Saos-2 cell, AGS cell, A549 cell, PANC-1 cell, U251 cell, HL-60 cell, SK-MEL-28 cell, DU145 cell, MDA-MB-231 cell, PC-3 cell, from Shanghai Medicilon Ltd., were placed in a 37° C., 5% $CO_2$ cell incubator, and cultured in DMEM culture medium with 10% FBS (Saos-2 cell, U251 cell, HeLa cell, A549 cell, PANC-1 cell, SK-MEL-28 cell, MDA-MB-231 cell), or in DMEM culture medium with 10% FBS (A549 cell, PANC-1 cell), or in IMDM culture medium with 20% FBS (HL-60 cell), or in RPMI1640 culture medium with 20% FBS (OVCAR-3 cell), or in F12 culture medium with 10% FBS (AGS, DU145 cell), or in F12 culture medium with 10% FBS (PC-3 cell), or in RPMI1640 culture medium with 10% FBS (Jurkat E6-1 cell).

Test II. General Materials and Methods

Phenethyl isothiocyanate, cyclohexyl isothiocyanate, benzyl isothiocyanate; Axitinib, erlotinib, imatinib, nilotinib, pazopanib, sorafenib, everolimus, arsenic trioxide, bortezomib, romidepsin, vorinostat, Vemurafenib, methotrexate.

Cell culture: 786-0 cell, PANC-1 cell, HL-60 cell, A549 cell, Saos-2 cell, Jurkat E6-1 cell, SK-MEL-28 cell, HT29 cell, from Shanghai Medicilon Ltd., were placed in a 37° C., 5% $CO_2$ cell incubator, and cultured in RPMI1640 culture medium with 10% FBS (786-0 cell, Jurkat E6-1 cell), or in DMEM culture medium with 10% FBS (A549, PANC-1, SK-MEL-28, HT29 cell), or in IMDM culture medium with 20% FBS (HL-60 cell).

Test III. General Experimental Materials and Methods

Phenethyl isothiocyanate, cyclohexyl isothiocyanate, 4-chloro-benzyl isothiocyanate, sulforaphane, trityl isothiocyanate (Trityl), phenethyl isothiocyanate-N-acetylcysteine adduct (PEITC-NAC), 4-phenylbutyl isothiocyanate (PBITC), 6-phenyl-hexyl isothiocyanate (PHITC), 3-phenyl propyl isothiocyanate (3-phenylpropyl ITC), phenylpropyl isothiocyanate (PPITC), 4-chloro-benzyl isothiocyanate (4-chlorobenzyl), ethyl phenyl isothiocyanate (L-alpha-methylbenzyl), benzyl isothiocyanate (BITC); abiraterone, Enzalutamide, leuprolide, bicalutamide.

Cell culture: Androgen-dependent human prostate cancer cells LNCaP, from Shanghai Medicilon Ltd., were placed in a 37° C., 5% $CO_2$ cell incubator, and were cultured in RPMI1640 culture medium with 10% FBS. Androgen-independent human prostate cancer cells DU145, PC-3, from Shanghai Medicilon Ltd., were placed in a 37° C., 5% $CO_2$ cell incubator, and were cultured in F12 culture medium with 10% FBS.

$IC_{50}$ of Drug Acting on Cells:

isothiocyanates or derivatives thereof and DNA-effecting or influencing anticancer drugs, kinase-inhibiting anticancer drugs or hormonal anticancer drugs for endocrine therapy were administered separately or in combination to cancer cells. Cells were seeded into 384-well plates, and cultured for 24 hours in a $CO_2$ incubator. Drugs were dissolved in DMSO and diluted to 9 concentration-gradients in 96 well plates, and then added to corresponding cells in 384-well plates, in which the concentrations of DMSO in 384 well plates were less than 1%. Triplicate wells were set for each concentration. After administration, the cells were cultured in the $CO_2$ incubator for another 72 hrs, and afterwards, cell viability was tested by using CellTiter-Glo® reagent and luminescence detector. And $IC_{50}$ values of each administration group were calculated.

Calculation of Synergy Effect of Drugs:

Interactions between two drugs (synergistic, additive, antagonism) are defined according to combination index CI value.

CI value was calculated by the following formula: $CI = (Am)_{50}/(As)_{50} + (Bm)_{50}/(Bs)_{50}$, $(Am)_{50}$ represents the concentration of drug A needed for 50% inhibition ($IC_{50}$) when used in combination;

$(As)_{50}$ represents the concentration of drug A needed for 50% inhibition (IC50) when used alone;

$(Bm)_{50}$ represents the concentration of drug B needed for 50% inhibition ($IC_{50}$) when used in combination;

$(Bs)_{50}$ represents the concentration of drug B needed for 50% inhibition ($IC_{50}$) when used alone.

CI value>1 indicates antagonism effect, =1 represents additive effect, <1 indicates synergy effect.

The method of calculating $(Am)_{50}$ and $(Bm)_{50}$:

9 concentration gradients of drug A were set (A1, A2, A3, A4, A5, A6, A7, A8, A9); 9 concentration gradients of drug B were set (B1, B2, B3, B4, B5, B6, B7, B8, B9); and each concentration one-to-one corresponds to another concentration from high concentration to low concentration; A and B were administrated in combination to the corresponding cells in the 384 well plate, wherein into cell well 1 was added drug (A1+B1), into cell well 2 was added drug (A2+B2), into cell well 3 was added drug (A3+B3), . . . and into cell well 9 was added drug (A9+B9). Triplicate wells were set for each co-administration cell well.

After administration, cells were cultured in the $CO_2$ incubator for another 72 hrs, and afterwards, cell viability was tested by using CellTiter-Glo® reagent and luminescence detector. Curves were plotted according to concentrations or logarithm concentrations of drug A vs cell inhibition rate in the corresponding cell well, and $IC_{50}$, i.e. $(Am)_{50}$ was calculated. Curves were plotted according to concentration or logarithm concentration of drug B vs cell inhibition rate in the corresponding cell well, and $IC_{50}$, i.e. $(Bm)_{50}$ was calculated.

Calculation of $(As)_{50}$:

9 concentration gradients of drug A were set (A1, A2, A3, A4, A5, A6, A7, A8, A9), and administrated alone to the corresponding cells in the 384 well plate, and triplicate wells were set for each administration concentration. After administration, the cells were cultured in the $CO_2$ incubator for another 72 hrs, and afterwards, cell viability was tested by using CellTiter-Glo® reagent and luminescence detector. Curves were plotted according to concentration or logarithm concentration of drug A vs the cell inhibition rate in the corresponding cell well, and $IC_{50}$, i.e. $(As)_{50}$ was calculated.

Calculation of $(Bs)_{50}$:

9 concentration gradients of drug B were set (B1, B2, B3, B4, B5, B6, B7, B8, B9), and administrated alone to the corresponding cells in the 384 well plate, and triplicate wells were set for each administration concentration. After administration, the cells were cultured in the $CO_2$ incubator for another 72 hrs, and afterwards, cell viability was tested by using CellTiter-Glo® reagent and luminescence detector. Curves were plotted according to concentration or logarithm concentration of drug B vs the cell inhibition rate in the corresponding cell well, and $IC_{50}$, i.e. $(Bs)_{50}$ was calculated.

Experiment 1

Example 1: DNA-Effecting or Influencing Anticancer Drugs and Isothiocyanates have a Synergistic Effect on Inhibiting the Growth of Cancer Cells

TABLE 1

Bleomycin and different isothiocyanates act on HeLa cells

| mode of administration | $IC_{50}(\mu M)$ | | | | CI |
|---|---|---|---|---|---|
| | $(Am)_{50}$ | $(Bm)_{50}$ | $(As)_{50}$ | $(Bs)_{50}$ | |
| Phenethyl isothiocyanate (A) + Bleomycin (B) | 7.632 | 2.33 | 16.14 | >100 | <0.496 |
| Benzyl isothiocyanate (A) + Bleomycin (B) | 7.396 | 4.376 | 14.71 | 24.47 | 0.682 |
| cyclohexyl isothiocyanate (A) + Bleomycin (B) | 17.23 | 5.937 | 53.85 | 24.47 | 0.563 |

It can be seen from table 1 that the combination of Bleomycin and Phenethyl isothiocyanate, Benzyl isothiocyanate or cyclohexyl isothiocyanate has a synergistic effect on HeLa cells.

TABLE 2 bendamustine and different isothiocyanates act on Jurkat E6-1 cells

| mode of administration | $IC_{50}(\mu M)$ | | | | CI |
|---|---|---|---|---|---|
| | $(Am)_{50}$ | $(Bm)_{50}$ | $(As)_{50}$ | $(Bs)_{50}$ | |
| Phenethyl isothiocyanate (A) + bendamustine (B) | 9.009 | 2.201 | 12.1 | >100 | <0.756 |
| cyclohexyl isothiocyanate (A) + bendamustine (B) | 25.32 | 22.67 | 42.05 | >100 | <0.715 |

It can be seen from table 2 that the combination of Bendamustine and Phenethyl isothiocyanate or cyclohexyl isothiocyanate has a synergistic effect on JurkatE6-1 cells.

TABLE 3 cis-platinum and different isothiocyanates act on HeLa cells or OVCAR-3 cells

| mode of administration | cells | $IC_{50}$ ($\mu M$) | | | | CI |
|---|---|---|---|---|---|---|
| | | $(Am)_{50}$ | $(Bm)_{50}$ | $(As)_{50}$ | $(Bs)_{50}$ | |
| Phenethyl isothiocyanate (A) + cisplatin (B) | HeLa | 15.08 | 3.32 | 16.9 | 32.81 | 0.993 |
| Phenethyl isothiocyanate (A) + cisplatin (B) | OVCAR-3 | 7.205 | 0.7005 | 9.866 | 4.524 | 0.885 |
| Benzyl isothiocyanate (A) + cisplatin (B) | | 5.995 | 3.467 | 8.415 | 20.57 | 0.881 |
| cyclohexyl isothiocyanate (A) + cisplatin (B) | | 8.116 | 20.51 | 36.52 | 20.57 | 0.956 |

It can be seen from table 3 that the combination of cisplatin and Phenethyl isothiocyanate, Benzyl isothiocyanate or cyclohexyl isothiocyanate has a synergistic effect on HeLa cells or OVCAR-3 cells.

TABLE 4 cyclophosphamide and different isothiocyanates act on OVCAR-3 cells

| mode of administration | $IC_{50}(\mu M)$ | | | | CI |
|---|---|---|---|---|---|
| | $(Am)_{50}$ | $(Bm)_{50}$ | $(As)_{50}$ | $(Bs)_{50}$ | |
| Phenethyl isothiocyanate (A) + cyclophosphamide (B) | 11.33 | 5.136 | 31.83 | >100 | <0.407 |

It can be seen from table 4 that the combination of cyclophosphamide and Phenethyl isothiocyanate has a synergistic effect on OVCAR-3 cells.

TABLE 5 carboplatin and different isothiocyanates act on OVCAR-3 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + carboplatin (B) | 9.212 | 3.395 | 31.83 | 38.73 | 0.377 |
| Benzyl isothiocyanate (A) + carboplatin (B) | 6.594 | 11.73 | 18.17 | 58.85 | 0.562 |
| 4-chloro-benzyl isothiocyanate (A) + carboplatin (B) | 9.785 | 15.29 | 18.15 | 58.85 | 0.799 |
| L-ethyl phenyl isothiocyanate (A) + carboplatin (B) | 12.62 | 25.1 | 43.56 | 58.85 | 0.716 |

It can be seen from table 5 that the combination of carboplatin and phenethyl isothiocyanate, benzyl isothiocyanate, 4-chloro-benzyl isothiocyanate or L-ethyl phenyl isothiocyanate has a synergistic effect on OVCAR-3 cells.

TABLE 6 adriamycin and different isothiocyanates act on Saos-2 cells, AGS cells or OVCAR-3 cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| Phenethyl isothiocyanate (A) + adriamycin (B) | AGS | 1.11 | 0.04927 | 14.67 | 0.05345 | 0.997 |
| Phenethyl isothiocyanate (A) + adriamycin (B) | Saos-2 | 2.945 | 0.3469 | 20.49 | 0.8992 | 0.5295 |
| Benzyl isothiocyanate (A) + adriamycin (B) | | 1.639 | 0.3279 | 14.53 | 0.5739 | 0.684 |
| cyclohexyl isothiocyanate (A) + adriamycin (B) | | 3.57 | 0.357 | 66.04 | 0.5739 | 0.676 |
| Phenethyl isothiocyanate (A) + adriamycin (B) | OVCAR-3 | 3.574 | 0.5109 | 31.83 | 1.74 | 0.406 |

It can be seen from table 6 that the combination of adriamycin and phenethyl isothiocyanate, benzyl isothiocyanate or cyclohexyl isothiocyanate has a synergistic effect on Saos-2 cells, AGS cells or OVCAR-3 cells.

TABLE 7 dacarbazine and different isothiocyanates act on SK-MEL-28 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + dacarbazine (B) | 24.14 | 23.69 | 32.68 | >100 | <0.976 |

It can be seen from table 7 that the combination of dacarbazine-28 and Phenethyl isothiocyanate has a synergistic effect on SK-MEL-28 cells.

TABLE 8 topotecan and different isothiocyanates act on HeLa cells or OVCAR-3 cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| Phenethyl isothiocyanate (A) + topotecan (B) | OVCAR-3 | 0.3639 | 0.04483 | 9.866 | 0.07737 | 0.616 |

TABLE 8-continued topotecan and different isothiocyanates act on HeLa cells or OVCAR-3 cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| Phenethyl isothiocyanate (A) + topotecan (B) | HeLa | 4.593 | 0.7811 | 24.64 | 1.547 | 0.691 |
| Benzyl isothiocyanate (A) + topotecan (B) | | 1.643 | 0.108 | 14.71 | 0.5799 | 0.298 |
| cyclohexyl isothiocyanate (A) + topotecan (B) | | 0.7541 | 0.1297 | 23.24 | 0.2024 | 0.673 |

It can be seen from table 8 that the combination of topotecan and Phenethyl isothiocyanate, Benzyl isothiocyanate or cyclohexyl isothiocyanate has a synergistic effect on HeLa cells or OVCAR-3 cells.

TABLE 9 fludarabine and different isothiocyanates act on HL-60 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + fludarabine (B) | 4.368 | 0.1268 | 6.265 | 1.571 | 0.778 |

It can be seen from table 9 that the combination of fludarabine and Phenethyl isothiocyanate has a synergistic effect on HL-60 cells.

TABLE 10 gemcitabine and different isothiocyanates act on A549cells, OVCAR-3 cells or PANC-1 cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| Phenethyl isothiocyanate (A) + gemcitabine (B) | A549 | 13.3 | 1.239 | 22.04 | 9.541 | 0.733 |
| Phenethyl isothiocyanate (A) + gemcitabine (B) | OVCAR-3 | 10.63 | 4.52 | 31.83 | 89.7 | 0.384 |
| Phenethyl isothiocyanate (A) + gemcitabine (B) | PANC-1 | 6.151 | 1.513 | 19.57 | 11.49 | 0.446 |
| sulforaphane (A) + gemcitabine (B) | | 7.171 | 2.202 | 14.33 | 10.7 | 0.706 |
| trityl isothiocyanate (A) + gemcitabine (B) | | 15.26 | 12.71 | >50 | 32.36 | <0.698 |
| Phenethyl isothiocyanate-N-acetylcysteine adduct (A) + gemcitabine (B) | | 8.206 | 3.011 | 28.59 | 32.36 | 0.380 |
| 4-Phenbutyl isothiocyanate (A) + gemcitabine (B) | | 7.01 | 2.088 | 26.87 | 32.36 | 0.325 |
| 6-Phenhexyl isothiocyanate (A) + gemcitabine (B) | | 7.491 | 2.437 | 30.91 | 32.36 | 0.318 |
| Phenylpropyl isothiocyanate (A) + gemcitabine (B) | | 6.228 | 1.587 | 35.11 | 32.36 | 0.226 |

TABLE 10-continued gemcitabine and different isothiocyanates act on A549cells, OVCAR-3 cells or PANC-1 cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| 4-chloro-benzyl isothiocyanate (A) + gemcitabine (B) | | 10.46 | 5.294 | 34.05 | 32.36 | 0.471 |
| 4-methoxy-benzyl isothiocyanate (A) + gemcitabine (B) | | 6.586 | 1.807 | 11.28 | 32.36 | 0.6397 |
| cyclohexyl isothiocyanate (A) + gemcitabine (B) | | 9.786 | 4.532 | 193.4 | 32.36 | 0.191 |
| L-ethyl phenyl isothiocyanate (A) + gemcitabine (B) | | 7.902 | 2.758 | 24 | 32.36 | 0.414 |
| Phenyl isothiocyanate (A) + gemcitabine (B) | | 14.14 | 15.97 | 77.19 | 32.36 | 0.644 |
| Benzyl isothiocyanate (A) + gemcitabine (B) | | 6.901 | 2.014 | 23.42 | 32.36 | 0.3569 |
| allyl isothiocyanate (A) + gemcitabine (B) | | 8.017 | 2.852 | 115.8 | 32.36 | 0.1574 |

It can be seen from table 10 that the combinations of gemcitabine and isothiocyanates such as phenethyl isothiocyanate have a synergistic effect on A549 cells, OVCAR-3 cells or PANC-1 cells.

TABLE 11

Lomustine and different isothiocyanates act on U251 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Lomustine (B) | 11.9 | 5.6 | 20.9 | 65.4 | 0.655 |
| cyclohexyl isothiocyanate (A) + Lomustine (B) | 35.31 | 38.4 | 71.14 | 115.3 | 0.829 |

It can be seen from table 11 that the combination of Lomustine and phenethyl isothiocyanate or cyclohexyl isothiocyanate has a synergistic effect on U251 cells.

TABLE 12

Nelarabine and different isothiocyanates act on Jurkat E6-1 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Nelarabine (B) | 1.751 | 0.123 | 11.62 | 55.49 | 0.1529 |
| cyclohexyl isothiocyanate (A) + Nelarabine (B) | 25.56 | 23.01 | 42.05 | >200 | <0.723 |

It can be seen from table 12 that the combination of Nelarabine and Phenethyl isothiocyanate or cyclohexyl isothiocyanate has a synergistic effect on JurkatE6-1 cells.

TABLE 13 daunorubicin and different isothiocyanates act on HL-60 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + daunorubicin (B) | 0.003345 | 0.0002909 | 7.618 | 0.02639 | 0.0115 |
| Benzyl isothiocyanate (A) + daunorubicin (B) | 0.7773 | 0.06804 | 11.47 | 0.2361 | 0.356 |
| cyclohexyl isothiocyanate (A) + daunorubicin (B) | 0.8148 | 0.07331 | 52.67 | 0.2361 | 0.326 |

It can be seen from table 13 that the combination of daunorubicin and phenethyl isothiocyanate, benzyl isothiocyanate or cyclohexyl isothiocyanate has a synergistic effect on HL-60 cells.

TABLE 14

Cabazitaxel and phenylethyl isothiocyanates act on DU145 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Cabazitaxel (B) | 8.841 | 0.008519 | 42.15 | 0.02653 | 0.531 |

It can be seen from table 14 that the combination of Cabazitaxel and Phenethyl isothiocyanate has a synergistic effect on DU145 cells.

TABLE 15 docetaxel and isothiocyanates act on Human breast cancer
MDA-MB-231 cells or human gastric cancer AGS cells

| mode of administration | cells | IC$_{50}$ (μM) | | | | CI |
|---|---|---|---|---|---|---|
| | | (Am)$_{50}$ | (Bm)$_{50}$ | (As)$_{50}$ | (Bs)$_{50}$ | |
| Phenethyl isothiocyanate (A) + docetaxel (B) | MDA-MB-231 | 6.847 | 0.08031 | 25.12 | 1.248 | 0.337 |
| Benzyl isothiocyanate (A) + docetaxel (B) | | 8.74 | 0.01898 | 11.38 | 0.3914 | 0.8165 |
| cyclohexyl isothiocyanate (A) + docetaxel (B) | | 18.88 | 0.02136 | 37.54 | 0.3914 | 0.5575 |
| Phenethyl isothiocyanate (A) + docetaxel (B) | AGS | 0.8909 | 0.00007355 | 11.75 | 0.009735 | 0.0834 |

It can be seen from table 15 that the combination of docetaxel and phenethyl isothiocyanate, benzyl isothiocyanate or cyclohexyl isothiocyanate has a synergistic effect on human breast cancer MDA-MB-231 cells or the combination of docetaxel and phenethyl isothiocyanate has a synergistic effect on human gastric cancer AGS cells.

TABLE 16 docetaxel and phenethyl isothiocyanate act on Human breast cancer MDA-MB-231 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Paclitaxel (B) | 3.147 | 0.0004961 | 20.46 | 0.01995 | 0.179 |

It can be seen from table 16 that the combination of docetaxel and phenethyl isothiocyanate has a synergistic effect on human breast cancer MDA-MB-231 cells.

TABLE 17 vincristine sulfate and isothiocyanates act on human leukemia HL-60 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Benzyl isothiocyanate (A) + vincristine sulfate (B) | 0.4527 | 0.0009014 | 11.47 | 0.01262 | 0.111 |
| cyclohexyl isothiocyanate (A) + vincristine sulfate (B) | 0.4921 | 0.001094 | 52.67 | 0.01262 | 0.096 |

It can be seen from table 17 that the combination of vincristine sulfate and benzyl isothiocyanate or cyclohexyl isothiocyanate has a synergistic effect on human leukemia HL-60 cells.

TABLE 18 vinblastine sulfate and phenylethyl isothiocyanates act on human leukemia HL-60 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + vincristine sulfate (B) | 5.559 | 0.004944 | 6.663 | 0.1871 | 0.8607 |

It can be seen from table 18 that the combination of vinblastine sulfate and phenylethyl isothiocyanate has a synergistic effect on human leukemia HL-60 cells.

Experiment II

Example 2: Kinase-Inhibiting Anticancer Drugs and Isothiocyanates have a Synergistic Effect in Inhibiting the Growth of Cancer Cells

TABLE 19

IC$_{50}$ and CI value of combined effect of Axitinib and different isothiocyanates acting on human leukemia kidney cancer cells 786-O

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Axitinib (B) | 11.91 | 0.62 | 15.97 | 5.51 | 0.858 |
| Benzyl isothiocyanate (A) + Axitinib (B) | 6.642 | 1.843 | 13.21 | 26.06 | 0.5735 |
| cyclohexyl isothiocyanate (A) + Axitinib (B) | 27.53 | 10 | 106.6 | 26.06 | 0.642 |

It can be seen from the above table that the combination of Kinase-inhibiting drug Axitinib and phenethyl isothiocyanate, benzyl isothiocyanate or cyclohexyl isothiocyanate has a synergistic effect on human leukemia kidney cancer cells 786-O.

TABLE 20

IC$_{50}$ and CI value of combined effect of erlotinib and different isothiocyanates acting on pancreatic cancer cells PANC-1

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + erlotinib (B) | 13.54 | 7.329 | 19.57 | more than 100 | <0.765 |

It can be seen from the above table that the combination of kinase-inhibiting drug erlotinib and phenethyl isothiocyanate has a synergistic effect on pancreatic cancer cells PANC-1.

TABLE 21

IC$_{50}$ and CI value of combined effect of imatinib and different isothiocyanates acting on Leukemia cells HL-60

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + imatinib (B) | 5.01 | 2.608 | 6.663 | 12.14 | 0.967 |
| Benzyl isothiocyanate (A) + imatinib (B) | 4.696 | 4.696 | 11.47 | 22.51 | 0.618 |
| cyclohexyl isothiocyanate (A) + imatinib (B) | 17.1 | 8.549 | 52.67 | 22.51 | 0.542 |

It can be seen from the above table that the combination of kinase-inhibiting anticancer drug imatinib and phenethyl isothiocyanate, benzyl isothiocyanate or cyclohexyl isothiocyanate has a synergistic effect on Leukemia cells HL-60.

TABLE 22

IC$_{50}$ and CI value of combined effect of nilotinib and different isothiocyanates acting on Leukemia cells HL-60

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + nilotinib (B) | 3.476 | 0.106 | 6.265 | 4.435 | 0.579 |
| Benzyl isothiocyanate (A) + nilotinib (B) | 3.749 | 1.647 | 11.47 | 3.898 | 0.749 |
| cyclohexyl isothiocyanate (A) + nilotinib (B) | 5.45 | 2.981 | 52.67 | 3.898 | 0.868 |

It can be seen from the above table that the combination of kinase-inhibiting anticancer drug nilotinib and phenethyl isothiocyanate, benzyl isothiocyanate or cyclohexyl isothiocyanate has a synergistic effect on Leukemia cells HL-60.

TABLE 23

IC$_{50}$ and CI value of combined effect of Pazopanib and different isothiocyanates acting on human leukemia kidney cancer cells 786-O

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Pazopanib (B) | 11.5 | 1.32 | 15.97 | 106 | 0.732 |
| Benzyl isothiocyanate (A) + Pazopanib (B) | 7.609 | 4.632 | 13.21 | 198.8 | 0.559 |
| cyclohexyl isothiocyanate (A) + Pazopanib (B) | 28.09 | 15.79 | 106.6 | 198.8 | 0.343 |

It can be seen from the above table that the combination of Kinase-inhibiting anticancer drug Pazopanib and phenethyl isothiocyanate, benzyl isothiocyanate or cyclohexyl isothiocyanate has a synergistic effect on human leukemia kidney cancer cells 786-O.

TABLE 24

IC$_{50}$ and CI value of combined effect of Sorafenib and different isothiocyanates acting on human leukemia kidney cancer cells 786-O

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Sorafenib (B) | 10.6 | 1.32 | 15.97 | 6.99 | 0.853 |

It can be seen from the above table that the combination of kinase-inhibiting drug Sorafenib and phenethyl isothiocyanate has a synergistic effect on human leukemia kidney cancer cells 786-O.

TABLE 25

IC$_{50}$ and CI value of combined effect of everolimus and phenethyl isothiocyanate acting on U251 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + everolimus (B) | 6.7 | 1.8 | 20.9 | 23.7 | 0.3965 |

It can be seen from the above table that the combination of kinase-inhibiting drug Everolimus and phenethyl isothiocyanate has a synergistic effect on U251 cells.

TABLE 26

IC$_{50}$ and CI value of combined effect of arsenic trioxide and phenethyl isothiocyanate acting on HL-60 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + arsenic trioxide (B) | 3.69 | 0.5447 | 6.663 | 2.755 | 0.752 |

It can be seen from the above table that the combination of arsenic trioxide and phenethyl isothiocyanate has a synergistic effect on HL-60 cells.

TABLE 27

IC$_{50}$ and CI value of combined effect of bortezomib and phenethyl isothiocyanate acting on Saos-2 cells

| mode of administration | IC50 (μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + bortezomib (B) | 3.76 | 0.5665 | 20.49 | 0.8071 | 0.884 |

It can be seen from the above table that the combination of bortezomib and phenethyl isothiocyanate has a synergistic effect on Saos-2 cells.

TABLE 28

IC$_{50}$ and CI value of combined effect of Romidepsin and phenethyl isothiocyanate acting on Jurkat E6-1 cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + Romidepsin (B) | 5.983 | 0.0008488 | 12.09 | 0.002012 | 0.917 |

It can be seen from the above table that the combination of Romidepsin and phenethyl isothiocyanate has a synergistic effect on Jurkat E6-1 cells.

TABLE 29

IC$_{50}$ and CI value of combined effect of Vorinostat and phenethyl isothiocyanate acting on Jurkat E6-1 cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + Vorinostat (B) | 3.977 | 0.5065 | 11.47 | 1.228 | 0.759 |

It can be seen from the above table that the combination of Vorinostat and phenethyl isothiocyanate has a synergistic effect on Jurkat E6-1 cells.

TABLE 30

IC$_{50}$ and CI value of combined effect of Vemurafenib and phenethyl isothiocyanate acting on SK-MEL-28 cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + Vemurafenib (B) | 5.286 | 1.1 | 32.68 | 1.2 | 1.078 |

It can be seen from the above table that the combination of Vemurafenib and phenethyl isothiocyanate has an additive effect on SK-MEL-28 cells.

Experiment III

Example 3: Isothiocyanates and Hormonal Anti-Cancer Drugs for Endocrine Therapy have a Synergistic Effect in Inhibiting the Growth of Hormone-Dependent Prostate Cancer Cells

TABLE 31

IC$_{50}$ and CI value of combined effect of Abiraterone and different isothiocyanates acting on LNCaP cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + Abiraterone (B) | 12.17 | 5.921 | 20.44 | 26.91 | 0.815 |
| cyclohexyl isothiocyanate (A) + Abiraterone (B) | 17.83 | 11.79 | 53.96 | 21.15 | 0.888 |
| 4-chloro-benzyl isothiocyanate (A) + Abiraterone (B) | 12.36 | 5.034 | 17.28 | 21.15 | 0.953 |

It can be seen from table 31 that the combination of hormonal anti-prostate cancer drug Abiraterone and phenethyl isothiocyanate, cyclohexyl isothiocyanate or 4-chlorobenzyl isothiocyanate has a synergistic effect on hormone-dependent prostate cancer cells LNCaP.

TABLE 32

IC$_{50}$ and CI value of combined effect of Enzalutamide and different isothiocyanates acting on LNCaP cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + Enzalutamide (B) | 14.62 | 8.548 | 20.44 | 69.71 | 0.838 |
| Benzyl isothiocyanate (A) + Enzalutamide (B) | 12.96 | 11.76 | 18.5 | 124.2 | 0.795 |

It can be seen from table 32 that the combination of hormonal anti-prostate cancer drug Enzalutamide and phenethyl isothiocyanate or benzyl isothiocyanate has a synergistic effect on hormone-dependent prostate cancer cells LNCaP.

TABLE 33

IC$_{50}$ and CI value of combined effect of leuprorelin and different isothiocyanates acting on LNCaP cells

| mode of administration | IC$_{50}$(μM) | | | | CI |
| --- | --- | --- | --- | --- | --- |
| | (Am)$_{50}$ | (Bm)$_{50}$ | (As)$_{50}$ | (Bs)$_{50}$ | |
| Phenethyl isothiocyanate (A) + leuprorelin (B) | 17.66 | 12.48 | 20.44 | 322.8 | 0.903 |

It can be seen from table 33 that the combination of hormonal anti-prostate cancer drug leuprorelin and phenethyl isothiocyanate has a synergistic effect on hormone-dependent prostate cancer cells LNCaP.

TABLE 34

IC$_{50}$ and CI value of combined effect of Bicalutamide and different isothiocyanates acting on LNCaP cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Bicalutamide (B) | 15.99 | 1.988 | 27.82 | 70.01 | 0.603 |
| Sulforaphane (A) + Bicalutamide (B) | 3.988 | 1.901 | 15.32 | 72.51 | 0.287 |
| trityl isothiocyanate (A) + Bicalutamide (B) | 14.42 | 10.31 | 238.3 | 72.51 | 0.203 |
| Phenethyl isothiocyanate acetylcysteine adducts (A) + Bicalutamide (B) | 3.158 | 1.574 | 16.41 | 72.51 | 0.214 |
| 4-Phenbutyl isothiocyanate (A) + Bicalutamide (B) | 2.09 | 0.847 | 17.51 | 72.51 | 0.131 |
| 6-Phenhexyl isothiocyanate (A) + Bicalutamide (B) | 2.677 | 1.14 | 18.8 | 72.51 | 0.158 |
| 3-Phenylpropyl isothiocyanate (A) + Bicalutamide (B) | 3.866 | 2.144 | 24.48 | 72.51 | 0.187 |
| Phenylpropyl isothiocyanate (A) + Bicalutamide (B) | 5.225 | 2.718 | 22.94 | 72.51 | 0.265 |
| 4-chloro-benzyl isothiocyanate (A) + Bicalutamide (B) | 2.38 | 0.9355 | 17.28 | 72.51 | 0.1506 |
| Phenyl isothiocyanate (A) + Bicalutamide (B) | 10.17 | 40.66 | 43.55 | 70.01 | 0.814 |
| Benzyl isothiocyanate (A) + Bicalutamide (B) | 10.63 | 42.53 | 32.21 | 70.01 | 0.9375 |

It can be seen from table 34 that the combination of hormonal anti-prostate cancer drug Bicalutamide and phenethyl isothiocyanate, sulforaphane, trityl isothiocyanate, phenethyl isothiocyanate-N-acetyl-cysteine adducts, 4-phenyl-butyl isothiocyanate, 6-phenyl-hexyl isothiocyanate acetate, 3-phenylpropyl isothiocyanate, phenylpropyl isothiocyanate, 4-chloro-benzyl isothiocyanate, phenyl isothiocyanate, benzyl isothiocyanate has a synergistic effect on hormone-dependent prostate cancer cells LNCaP.

Example 4: Isothiocyanates and Hormonal Anti-Cancer Drugs for Endocrine Therapy have a Synergistic Effect in Inhibiting the Growth of Hormone-Independent Prostate Cancer Cells

TABLE 35

IC$_{50}$ and CI value of combined effect of Abiraterone and phenethyl isothiocyanates acting on DU145 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Abiraterone (B) | 8.978 | 3.224 | 19.37 | 37.39 | 0.550 |

TABLE 36

IC$_{50}$ and CI value of combined effect of Abiraterone and phenethyl isothiocyanates acting on PC-3 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Abiraterone (B) | 29.31 | 15.84 | 52.56 | 100.8 | 0.715 |

It can be seen from tables 35 and 36 that the combination of hormonal anti-prostate cancer drug Abiraterone and phenethyl isothiocyanate has a synergistic effect on hormone-independent prostate cancer cells DU145 and PC-3.

TABLE 37

IC$_{50}$ and CI value of combined effect of Enzalutamide and phenethyl isothiocyanates acting on DU145 cells

| method of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Enzalutamide (B) | 9.988 | 3.99 | 19.24 | 331.8 | 0.531 |

TABLE 38

IC$_{50}$ and CI value of combined effect of Enzalutamide and phenethyl isothiocyanates acting on PC-3 cells

| mode of administration | IC$_{50}$(μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Enzalutamide (B) | 34.34 | 27.65 | 52.56 | >100 | >0.93 |

It can be seen from tables 37 and 38 that the combination of hormonal anti-prostate cancer drug Enzalutamide and phenethyl isothiocyanate has a synergistic effect on hormone-independent prostate cancer cells DU145 and PC-3.

TABLE 39

IC$_{50}$ and CI value of combined effect of Bicalutamide and phenethyl isothiocyanates acting on DU145 cells

| method of administration | IC$_{50}$ (μM) | | | | CI |
|---|---|---|---|---|---|
| | (Am)$_{50}$ | (Bm)$_{50}$ | (As)$_{50}$ | (Bs)$_{50}$ | |
| Phenethyl isothiocyanate (A) + Bicalutamide (B) | 17.03 | 11.6 | 19.37 | 130.2 | 0.968 |

It can be seen from table 39 that the combination of hormonal anti-prostate cancer drug Bicalutamide and phenethyl isothiocyanate has a synergistic effect on hormone-independent prostate cancer cell DU145.

Example 5: The Effect of the Combination of Phenethyl Isothiocyanate and Endocrine Therapy on Subjects with Advanced Prostate Cancer (1) Male volunteer, 61 years old By the end of March, 2011, he was diagnosed with advanced prostate cancer, PSA 145.4;

PEITC enhanced endocrine therapy began in April 2011: orally administrating Casodex (bicalutamide) 50 mg, 1 time/day, orally administrating PEITC 60 mg, 3 time/day, intramuscularly injecting Zoladex (goserelin) 3.6 mg, 1/28 days;

During Jul. 7, 2011 to Sep. 29, 2011, endocrine therapy was paused because of radiotherapy;

Sep. 30, 2011, the PEITC enhanced endocrine therapy was restarted;

Jun. 14, 2012, tPSA was lower than the limit of detection.

The pathological diagnosis results on Mar. 30, 2011: prostate biopsy was performed for 13 times, while the prostate cancer was shown at the 1st to 13th biopsy, Gleason scores 4+5 (sum9), and some has shown signet ring cell. The ratio of the tumor at the 1st, 2nd, 4th, 5th, 8th, 12th and 13th biopsy is more than ⅔, while more than ⅓ at the 3th and 6th biopsy, and less than ⅓ at the 7th, 9th to 11th biopsy.

The pathological diagnosis results on Sep. 13, 2012: prostate biopsy was performed for 13 times, while small glands irregular in the form can be seen in the prostate tissues. Some nuclei was enlarged, there is abnormal shapes, and immunohistochemistry suggested P504s (−), M630+++; suggesting that it was tissue degeneration associated with basal cell hyperplasia after endocrine therapy, no clear tumor tissue was found in the inspected organism, which should be considered in combination with clinical symptoms.

Immunohistochemistry: for the 1st, 2nd, 3rd and 4th biopsy, P504s(−), M630+++; for the 7th, 10th, 12th biopsy, P504s(−), M630+++, A/E1/3+++; the 8th biopsy, P504s(−), PsAp+, M630++, CK7+−.

(2) Male volunteer, 81 years old

By April, 2010, he was diagnosed with advanced prostate cancer, GS. (4+4);

Endocrine therapy was performed during April, 2010 to March, 2012, tPSA was reduced from 1035 to 0.48 (lowest), and then rose gradually to 126;

Chemotherapy was started on March, 2012; meanwhile, PEITC was orally administered at 60 mg, 3 times per day;

On June, 2016, the tPSA was reduced back to 0.102.

Comparative Example 1: Non-DNA Effecting or Influencing Anticancer Drugs and Isothiocyanates do not have a Synergistic Effect in Inhibiting the Growth of Cancer Cells

TABLE 40

| isothiocyanates and folic acid-targeting anti-cancer drug methotrexate act on A549 cells | | | | | |
|---|---|---|---|---|---|
| mode of administration | $IC_{50}(\mu M)$ | | | | |
| | $(Am)_{50}$ | $(Bm)_{50}$ | $(As)_{50}$ | $(Bs)_{50}$ | CI |
| Phenethyl isothiocyanate (A) + methotrexate (B) | 2.0 | 0.16 | 22.3 | 0.08 | 2.0897 |

It can be seen from table 40 that the combination of folic acid-targeting anti-cancer drug methotrexate and phenethyl isothiocyanate has an antagonism effect when acted on lung cancer cells A549.

Comparative Example 2: Non-Kinase Inhibiting Anticancer Drugs and Isothiocyanates do not have a Synergistic Effect in Inhibiting the Growth of Cancer Cells

TABLE 40

| Pralatrexate and phenethyl isothiocyanates act on Jurkat E6 cells | | | | | |
|---|---|---|---|---|---|
| mode of administration | $IC_{50}(\mu M)$ | | | | |
| | $(Am)_{50}$ | $(Bm)_{50}$ | $(As)_{50}$ | $(Bs)_{50}$ | CI |
| Phenethyl isothiocyanate (A) + Pralatrexate (B) | 7.067 | 0.0009941 | 12.1 | 0.001701 | 1.168 |

It can be seen from the above table that the combination of folic acid-targeting anti-cancer drug Pralatrexated and phenethyl isothiocyanate does not have a synergistic effect on lymphoma cells JurkatE6.

TABLE 42

| Leucovorin and phenethyl isothiocyanates act on HT29 cells | | | | | |
|---|---|---|---|---|---|
| mode of administration | $IC_{50}(\mu M)$ | | | | |
| | $(Am)_{50}$ | $(Bm)_{50}$ | $(As)_{50}$ | $(Bs)_{50}$ | CI |
| Phenethyl isothiocyanate (A) + Leucovorin (B) | 34.65 | 48.02 | 29.16 | >100 | >1.188 |

It can be seen from the above table that the combination of Leucovorin and phenethyl isothiocyanate does not have a synergistic effect on HT29 cells.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A composition, wherein the composition comprises:
   (A) a therapeutically effective amount of a first active ingredient, wherein the first active ingredient is an isothiocyanate selected from the group consisting of phenethyl isothiocyanate, sulforaphane phenethyl isothiocyanate acetylcysteine adducts, 4-phenbutyl isothiocyanate, 6-phenhexyl isothiocyanate, 3-phenylpropyl isothiocyanate, and 4-chloro-benzyl isothiocyanate;
   (B) a therapeutically effective amount of a second active ingredient, wherein the second active ingredient is bicalutamide.

2. The composition of claim 1, wherein a weight ratio of the first active ingredient to the second active ingredient is 1-10000: 10000-1.

3. The composition of claim 1, wherein a weight ratio of the first active ingredient to the second active ingredient is 1-1000: 1000-1.

4. A kit, wherein the kit comprises:
   (A) a first formulation comprising an isothiocyanate selected from the group consisting of phenethyl isothiocyanate, sulforaphane phenethyl isothiocyanate acetylcysteine adducts, 4-phenbutyl isothiocyanate, 6-phenhexyl isothiocyanate, 3-phenylpropyl isothiocyanate, and 4-chloro-benzyl isothiocyanate;
   (B) a second formulation comprising bicalutamide; and
   (C) instructions for use.

5. A combination of active ingredients, wherein the combination comprises the following ingredients, or is formed by combining the following ingredients:
- (A) a first active ingredient, wherein the first active ingredient is an isothiocyanate selected from the group consisting of phenethyl isothiocyanate, sulforaphane phenethyl isothiocyanate acetylcysteine adducts, 4-phenbutyl isothiocyanate, 6-phenhexyl isothiocyanate, 3-phenylpropyl isothiocyanate, and 4-chloro-benzyl isothiocyanate or a derivative thereof;
- (B) a second active ingredient, wherein the second active ingredient is bicalutamide.

6. A method of treating cancer, comprising: administering the composition of claim 1 to a subject in need, wherein the cancer is prostate cancer.

7. A pharmaceutical composition for treating cancer, wherein the pharmaceutical composition comprises:
- (A) a therapeutically effective amount of a first active ingredient, wherein the first active ingredient is an isothiocyanate selected from the group consisting of phenethyl isothiocyanate, sulforaphane phenethyl isothiocyanate acetylcysteine adducts, 4-phenbutyl isothiocyanate, 6-phenhexyl isothiocyanate, 3-phenylpropyl isothiocyanate, and 4-chloro-benzyl isothiocyanate;
- (B) a therapeutically effective amount of bicalutamide; and
- (C) a pharmaceutically acceptable carrier,
  - wherein a weight ratio of the first active ingredient to the second active ingredient is 1:10000 to 10000:1.

8. The pharmaceutical composition of claim 7, wherein the weight ratio of the first active ingredient to the second active ingredient is 1:1000 to 1000:1.

9. An in vitro non-therapeutic method of inhibiting growth of cancer cells, comprising adding the combination of active ingredients of claim 5 to inhibit the growth of cancer cells, wherein the cancer cells are prostate cancer cells.

10. A composition, wherein the composition comprises:
- (A) a therapeutically effective amount of a first active ingredient;
- (B) a therapeutically effective amount of a second active ingredient;
  - wherein the first active ingredient is selected from the group consisting of phenethyl isothiocyanate, cyclohexyl isothiocyanate, and 4-chloro-benzyl isothiocyanate, and the second active ingredient is Abiraterone, or
  - wherein the first active ingredient is selected from the group consisting of phenethyl isothiocyanate and benzyl isothiocyanate, and the second active ingredient is enzalutamide, or
  - wherein the first active ingredient is phenethyl isothiocyanate and the second active ingredient is leuprorelin, or
  - wherein the first active ingredient is selected from the group consisting of phenethyl isothiocyanate, sulforaphane, trityl isothiocyanate, phenethyl isothiocyanate acetylcysteine adducts, 4-phenbutyl isothiocyanate, 6-phenhexyl isothiocyanate, 3-phenylpropyl isothiocyanate, phenylpropyl isothiocyanate, 4-chloro-benzyl isothiocyanate, and benzyl isothiocyanate, and the second active ingredient is Bicalutamide.

* * * * *